US010315398B2

(12) United States Patent
Rapoport et al.

(10) Patent No.: US 10,315,398 B2
(45) Date of Patent: Jun. 11, 2019

(54) ARTICLES WITH CONFOUNDED EMISSION CHARACTERISTICS AND METHODS AND APPARATUS FOR THEIR AUTHENTICATION

(71) Applicant: HONEYWELL INTERNATIONAL INC., Morris Plains, NJ (US)

(72) Inventors: William Ross Rapoport, Bridgewater, NJ (US); Carsten Lau, Garbsen (DE); James Kane, Lawrenceville, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 107 days.

(21) Appl. No.: 15/430,194

(22) Filed: Feb. 10, 2017

(65) Prior Publication Data

US 2017/0154488 A1 Jun. 1, 2017

Related U.S. Application Data

(62) Division of application No. 13/584,026, filed on Aug. 13, 2012.

(Continued)

(51) Int. Cl.
*B32B 29/02* (2006.01)
*B32B 29/00* (2006.01)
(Continued)

(52) U.S. Cl.
CPC .............. *B32B 29/002* (2013.01); *B32B 3/10* (2013.01); *B32B 29/04* (2013.01); *B42D 25/00* (2014.10);
(Continued)

(58) Field of Classification Search
CPC .................................................... B29B 2/00
See application file for complete search history.

(56) References Cited

U.S. PATENT DOCUMENTS

| 4,451,530 A | 5/1984 | Kaule et al. |
| 7,487,919 B2 | 2/2009 | Giering et al. |

(Continued)

FOREIGN PATENT DOCUMENTS

| WO | 2007009756 A1 | 1/2007 |
| WO | 2009136921 A1 | 11/2009 |
| WO | 2011041657 A1 | 4/2011 |

OTHER PUBLICATIONS

International Search Report dated Jan. 29, 2013 in International Application No. PCT/2012/052491.
(Continued)

*Primary Examiner* — Yara B Green
(74) *Attorney, Agent, or Firm* — Lorenz & Kopf, LLP

(57) ABSTRACT

Embodiments include articles, authentication methods and apparatus, and article manufacturing methods. An article includes a substrate with a first luminescent taggant, and an extrinsic feature with a second luminescent taggant, which is positioned proximate a portion of the article surface. The first and second taggants produce emissions in overlapping emission bands as a result of exposure to excitation energy. Above the extrinsic feature, the substrate and extrinsic feature emissions combine in the overlapping emission band to produce "confounded" emissions that are distinguishable from the substrate emissions taken alone. An authentication system determines whether, in a region corresponding to a "substrate-only" region of an authentic article, emissions having first emission characteristics are detected in the overlapping emission band. The system also determines whether, in a region corresponding to an "extrinsic feature" region of an authentic article, the confounded emissions are detected in the overlapping emission band.

18 Claims, 5 Drawing Sheets

Related U.S. Application Data

(60) Provisional application No. 61/529,401, filed on Aug. 31, 2011.

(51) Int. Cl.

| | | |
|---|---|---|
| *B42D 25/21* | (2014.01) | |
| *B42D 25/40* | (2014.01) | |
| *B32B 3/10* | (2006.01) | |
| *C09K 11/77* | (2006.01) | |
| *B32B 29/04* | (2006.01) | |
| *G01N 21/64* | (2006.01) | |
| *B42D 25/29* | (2014.01) | |
| *B42D 25/00* | (2014.01) | |
| *B42D 25/382* | (2014.01) | |
| *B42D 25/387* | (2014.01) | |
| *G07D 7/1205* | (2016.01) | |

(52) U.S. Cl.
CPC ............ *B42D 25/21* (2014.10); *B42D 25/29* (2014.10); *B42D 25/382* (2014.10); *B42D 25/387* (2014.10); *B42D 25/40* (2014.10); *C09K 11/7769* (2013.01); *G01N 21/643* (2013.01); *G07D 7/1205* (2017.05); *B32B 2425/00* (2013.01); *B42D 2033/20* (2013.01); *B42D 2035/34* (2013.01); *G01N 2021/6421* (2013.01); *Y10T 428/24479* (2015.01)

(56) References Cited

U.S. PATENT DOCUMENTS

| | | |
|---|---|---|
| 7,597,961 B2 | 10/2009 | Maruvada et al. |
| 7,667,828 B2 | 2/2010 | Gibson |
| 7,790,056 B2 | 9/2010 | Giering et al. |
| 7,819,434 B2 | 10/2010 | Schwenk et al. |
| 7,927,511 B2 | 4/2011 | Giering et al. |
| 8,262,134 B2 | 9/2012 | Schwenk et al. |
| 8,263,948 B2 | 9/2012 | Rapoport et al. |
| 8,328,102 B2 | 12/2012 | Rapoport et al. |
| 8,330,122 B2 | 12/2012 | Smith et al. |
| 8,616,584 B2 | 12/2013 | Scholz et al. |
| 2005/0067489 A1* | 3/2005 | Jones .................. B41M 3/144 235/380 |
| 2007/0054067 A1 | 3/2007 | Power |
| 2007/0273141 A1 | 11/2007 | Schwenk |
| 2008/0116272 A1 | 5/2008 | Giering et al. |
| 2009/0033932 A1 | 2/2009 | Gibson |
| 2009/0051158 A1 | 6/2009 | Scholz |
| 2009/0141961 A1 | 6/2009 | Smith et al. |
| 2010/0140501 A1 | 6/2010 | Lawandy |
| 2013/0040150 A1 | 2/2013 | Trexler et al. |

OTHER PUBLICATIONS

Japanese Office Action for Application No. 2014-528495 dated Jun. 28, 2016.
Japanese Office Action for Application No. 2014-528495 dated Dec. 14, 2016.
Australian Examination Report No. 1 for Application No. 2012300280 dated Apr. 30, 2015.
Chinese Office Action for Application No. 201280052093.1 dated Jul. 21, 2015.
Chinese Office Action for Application No. 201280052093.1 dated May 18, 2016.
Chinese Office Action for Application No. 201280052093.1 dated Dec. 2, 2016.
European Search Report for Application No. 12827755.5-1704 / 2751548 dated Apr. 20, 2015.
Examination Report for Indian Patent Application No. 1273/DELNP/2014 dated Apr. 25, 2018.

* cited by examiner

US 10,315,398 B2

ARTICLES WITH CONFOUNDED EMISSION CHARACTERISTICS AND METHODS AND APPARATUS FOR THEIR AUTHENTICATION

CROSS-REFERENCE TO RELATED APPLICATIONS

This is a divisional of U.S. application Ser. No. 13/584,026, filed Aug. 13, 2012, which is related to and claims all available benefit of U.S. Provisional Patent Application 61/529,401 filed Aug. 31, 2011, the entire contents of which are herein incorporated by reference.

TECHNICAL FIELD

The present invention generally relates to radiation emitting compounds and methods and apparatus for their authentication.

BACKGROUND

A luminescent phosphor compound is a compound that is capable of emitting detectable quantities of radiation in the infrared, visible, and/or ultraviolet spectrums upon excitation of the compound by an external energy source. A typical luminescent phosphor compound includes at least a host material (e.g., a crystal lattice), an emitting ion (e.g., of a rare earth metal), and in some cases, a "sensitizing" ion (e.g., of a transition metal or of a different rare earth metal that can absorb and transfer the energy to the emitting rare earth metal ion). The production of radiation by a phosphor compound is accomplished by absorption of incident radiation by the emitting ion(s) or by either or both the host material and the sensitizing ion(s), energy transfer from the host material/sensitizing ion(s) to the emitting ion(s), and radiation of the transferred energy by the emitting ion(s).

The selected components of a phosphor compound may cause the compound to have particular emission properties, including specific wavelengths for its excitation energy, and specific spectral position(s) for higher spectral energy output emitted by the emitting ions of the phosphor compound ("emissions"). Not every ion will produce emissions in all host materials, however. There are many examples in which radiation that has the potential for emission is quenched, or the energy transfer from the absorbing ions or the host material to the emitting ions is so poor that the radiation effects are barely observable. In other host materials, the radiation effects can be very large and with quantum efficiency near unity.

For a specific phosphor compound that does produce observable emissions, the spectral position(s) of the higher spectral energy content (or luminescent output) in its emissions (i.e., its "spectral signature") may be used to uniquely identify the phosphor compound from other compounds. Primarily, the spectral signature is due to the rare earth ion(s). However, spectral perturbations may be present due to the influence of the host material on the various emitting ions, typically through crystal field strength and splitting. This holds true for the temporal behavior of the emissions, as well.

The unique spectral properties of some phosphor compounds make them well suited for use in authenticating or identifying articles of particular value or importance (e.g., banknotes, passports, biological samples, and so on). Accordingly, luminescent phosphor compounds with known spectral signatures have been incorporated into various types of articles to enhance the ability to detect forgeries or counterfeit copies of such articles, or to identify and track the articles. For example, luminescent phosphor compounds have been incorporated into various types of articles in the form of additives, coatings, and printed or otherwise applied features that may be analyzed in the process of authenticating or tracking an article.

An article that includes a luminescent phosphor compound may be authenticated using specially designed authentication equipment. More particularly, a manufacturer may incorporate a known phosphor compound (e.g., an "authenticating" phosphor compound) into its "authentic" articles. Authentication equipment configured to detect the authenticity of such articles would have knowledge (e.g., stored information and/or a variety of spectral filters) of the wavelengths of absorbable excitation energy and the spectral properties of emissions associated with the authenticating phosphor compound. When provided with a sample article for authentication, the authentication equipment exposes the article to excitation energy having wavelengths that correspond with the known wavelengths of absorption features of the luminescent phosphor compound that lead directly or indirectly to the desired emissions. The authentication equipment senses and characterizes the spectral parameters for any emissions that may be produced by the article. When the spectral signal of detected emissions is within the authenticating parameter range of the detection apparatus that corresponds with the authenticating phosphor compound (referred to as the "detection parameter space"), the article may be considered authentic. Conversely, when the authentication equipment fails to sense signals expected within the detection parameter space, the article may be considered unauthentic (e.g., a forged or counterfeited article).

The above-described techniques are highly effective at detecting and thwarting relatively unsophisticated forgery and counterfeiting activities. However, individuals with the appropriate resources and equipment may be able to employ spectrometry techniques in order to determine the components of some phosphor compounds. The phosphor compounds may then be reproduced and used with unauthentic articles, thus compromising the authentication benefits that may otherwise be provided by a particular phosphor compound. Accordingly, although a number of phosphor compounds have been developed to facilitate article authentication in the above-described manner, it is desirable to develop additional compounds, unique ways of using such compounds with articles, and techniques for authenticating articles, which may render forgery and counterfeiting activities more difficult, and/or which may prove beneficial for identifying and tracking articles of particular interest. Furthermore, other desirable features and characteristics of the present invention will become apparent from the subsequent detailed description of the invention and the appended claims, taken in conjunction with the accompanying drawings and this background of the invention.

BRIEF SUMMARY

An embodiment of an article comprises a substrate and an extrinsic feature. The substrate has a first surface and a first luminescent taggant. The first luminescent taggant produces substrate emissions in a substrate emission band when the substrate is exposed to substrate excitation energy. The extrinsic feature is positioned proximate a portion of the first surface. The extrinsic feature includes a second luminescent taggant that produces extrinsic feature emissions in an extrinsic feature emission band that at least partially overlaps the substrate emission band in an overlapping emission band when the extrinsic feature is exposed to extrinsic feature excitation energy. At the portion of the first surface, the substrate emissions and the extrinsic feature emissions combine in the overlapping emission band to produce confounded emissions that are distinguishable from the substrate emissions.

An embodiment of a method for authenticating an article that includes a substrate includes exposing a first surface of the substrate to excitation energy. The method further includes determining whether, in a first region of the first surface, first emissions having first emission characteristics are detected in a first emission band. The first emissions result from the excitation energy, and the first region corresponds to a region at which an extrinsic feature is not present in an authentic article. The method further includes determining whether, at a second region of the first surface, second emissions having second emission characteristics that are different from the first emission characteristics are detected in the first emission band. The second emissions result from the excitation energy, and the second region corresponds to a region at which the extrinsic feature is present in the authentic article.

An embodiment of an apparatus for authenticating an article comprises one or more excitation energy generators, one or more emissions detectors, and a processing system. The one or more excitation energy generators are configured to direct excitation energy toward a first surface of a substrate of the article. The emissions detector is configured to detect first emissions in a first emission band. The processing system is configured to determine whether, in a first region of the first surface, first emissions having first emission characteristics are detected in a first emission band. The first emissions result from the excitation energy, and the first region corresponds to a region at which an extrinsic feature is not present in an authentic article. The processing system is further configured to determine whether, at a second region of the first surface, second emissions having second emission characteristics that are different from the first emission characteristics are detected in the first emission band. The second emissions result from the excitation energy, and the second region corresponds to a region at which the extrinsic feature is present in the authentic article.

BRIEF DESCRIPTION OF THE DRAWINGS

Embodiments of the present invention will hereinafter be described in conjunction with the following figures, wherein like numerals denote like elements, and wherein.

DETAILED DESCRIPTION

Figure 1:
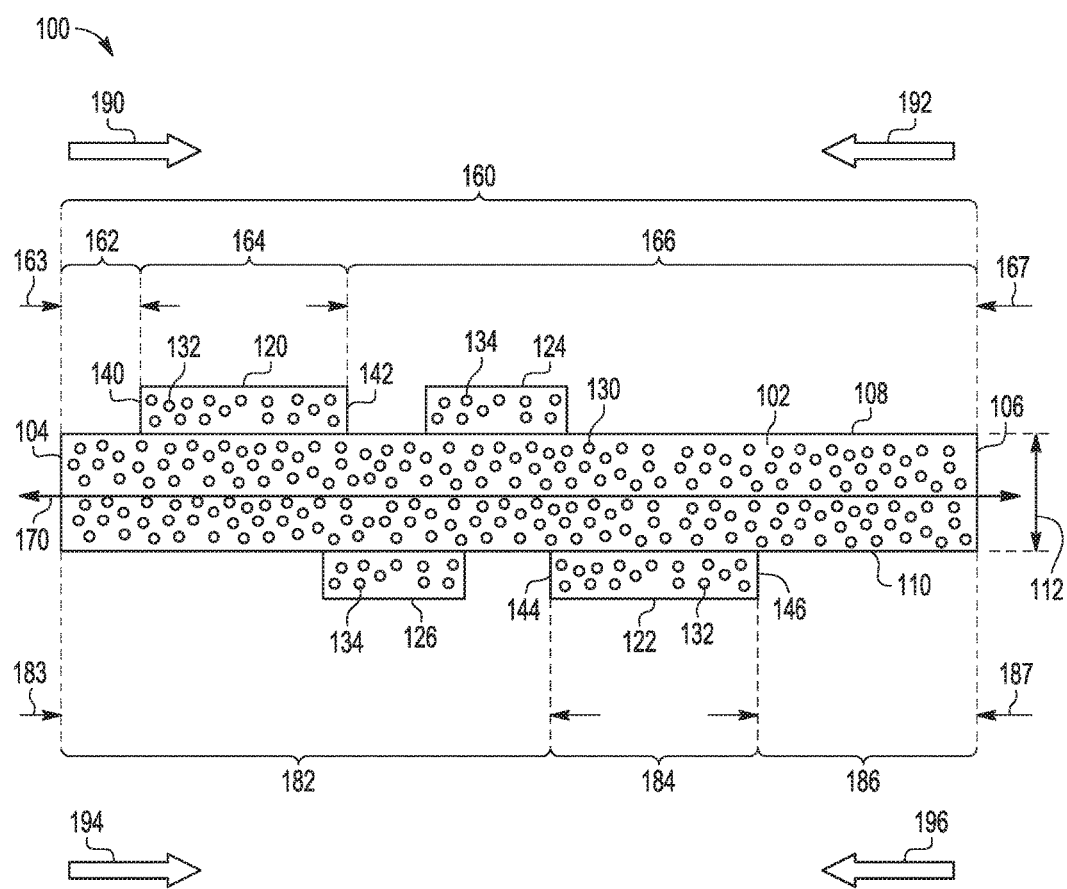
FIG. 1 is a cross-sectional, side view of an article that includes a substrate, an extrinsic feature, and an optional supplemental feature, according to an example embodiment.

The following detailed description of various embodiments of the invention is merely exemplary in nature and is not intended to limit the inventive subject matter or the application and uses of the inventive subject matter. Furthermore, there is no intention to be bound by any theory presented in the preceding background or the following detailed description.

Typically, producers of articles that include a substrate and a luminescent feature obtain the substrate material (e.g., paper) from one supplier, and the material for the luminescent feature (e.g., ink with a luminescent material) from a different supplier. "Uncontrolled" interaction between the substrate and the luminescent feature is undesirable, in that such interaction may alter the emission characteristics of the luminescent material and thus compromise the ability to produce articles that may be reliably authenticated. Accordingly, specifications for the substrate supplier and specifications for the luminescent feature material supplier include requirements that avoid such uncontrolled interaction. For example, specifications for the substrate supplier may stipulate that the substrate may not include materials that interfere with or modify the emissions that may be produced by the luminescent feature in one or more emission bands of interest. Such specifications enable the article producer to produce articles that may be reliably authenticated.

In contrast with the traditional practices discussed above, embodiments of the inventive subject matter include articles in which intentional, "controlled" interaction may occur between a substrate and an "extrinsic feature." More particularly, embodiments include articles incorporating luminescent materials, methods and apparatus for their authentication, and methods of their manufacture. As will be explained in detail below, according to an embodiment, an article includes a substrate and one or more extrinsic features, where the extrinsic feature(s) are formed from materials that are extrinsic from the substrate material, and the extrinsic feature(s) are applied to or embedded in the substrate. The substrate includes a first luminescent taggant, which produces substrate emissions in a substrate emission band when the substrate is exposed to appropriate excitation energy. The extrinsic feature (e.g., a printed, embedded or other type of feature) is located at or on a portion of the substrate, and includes a second luminescent taggant, which produces extrinsic feature emissions in an extrinsic feature emission band when the extrinsic feature is exposed to appropriate excitation energy.

The substrate emission band and the extrinsic feature emission band at least partially overlap, in an embodiment. Accordingly, at the portion of the substrate where a extrinsic feature is located, the substrate emissions and the extrinsic feature emissions combine in the overlapping emission band to produce "confounded emissions" that are distinguishable (e.g., in emission intensity, decay time constant, and/or other characteristics) from the substrate emissions alone. As will be explained in more detail below, an article may have additional features or characteristics that may be analyzed to definitively determine authenticity of the article.

According to various embodiments, methods and apparatus for authenticating such an article, which may include features such as those described above, include exposing various areas of the article to excitation energy at one or more wavelengths, and detecting emissions from the areas of the article within at least the overlapping emission band. More particularly, an area of the article at which an extrinsic feature is not present is exposed to the excitation energy, and emissions emanating from that area are detected (e.g., by a spectrally filtered photodetector that has response at that spectral band). In addition, an area of the article at which an extrinsic feature is present also is exposed to the excitation energy, and emissions emanating from that area are also detected. When the emissions from both areas are sufficiently different, the article may be identified as being authentic. Otherwise, the article is identified as being unauthentic. As will be explained in more detail below, additional analyses may be performed to definitively determine authenticity of the article.

Figure 2:
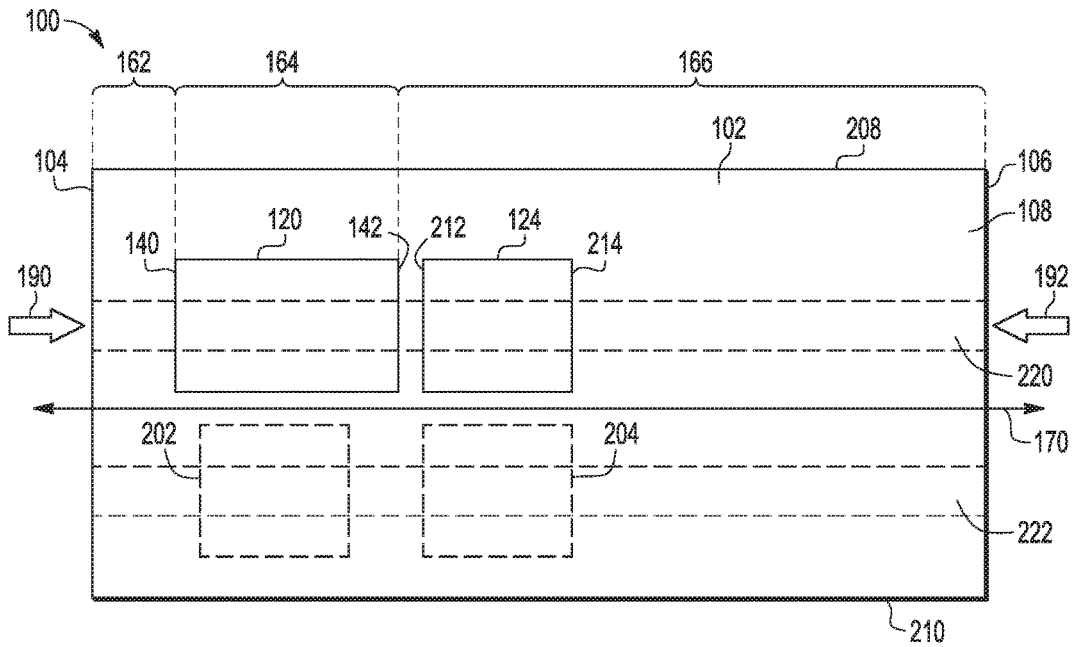
FIG. 2 is a top view of the article of FIG. 1, according to an example embodiment.

FIG. 1 is a cross-sectional, side view of an article 100 that includes a substrate 102, extrinsic features 120, 122, and optional "supplemental" features 124, 126, according to an example embodiment, and FIG. 2 is a top view of the article of FIG. 1 (i.e., a view of surface 108 of article 100). In various embodiments, article 100 may be any type of article selected from a group that includes, but is not limited to, an identification card, a driver's license, a passport, identity papers, a banknote, a check, a document, a paper, a stock certificate, a packaging component, a credit card, a bank card, a label, a seal, a postage stamp, a token (e.g., for use in gambling and/or with a gaming or vending machine), a liquid, a human, an animal, and a biological sample. Substrate 102 may be any of various types of substrates, and includes one or more materials selected from a group that includes, but is not limited to, paper, a polymer, glass, a metal, a textile, and a fiber. Accordingly, although article 100 is shown to be rectangular, in the embodiments of FIGS. 1 and 2, the example of a rectangular article is not meant to be limiting, and embodiments encompass articles having other shapes and configurations. Further, in the illustrated embodiment, article 100 is substantially planar in nature, although this is not a requirement.

Substrate 102, which may be rigid or flexible, may be formed from one or more layers or components, in various embodiments. The variety of configurations of substrate 102 are too numerous to mention, as the luminescent materials of the various embodiments may be used in conjunction with a vast array of different types of articles. Therefore, although a simple, unitary substrate 102 is illustrated in FIG. 1, it is to be understood that substrate 102 may have any of a variety of different configurations. For example, a substrate may be a "composite" substrate that includes a plurality of layers or sections of the same or different materials. For example, but not by way of limitation, a substrate may include one or more paper layers or sections and one or more plastic layers or sections that are laminated or otherwise coupled together to form the composite substrate (e.g., a paper layer/plastic layer/paper layer or plastic layer/paper layer/plastic layer composite substrate). In addition, although inanimate, solid articles are discussed herein, it is to be understood that an "article" also may include a human, an animal, a biological specimen, a liquid sample, and virtually any other object or material into or onto which a luminescent material of an embodiment may be included.

According to a particular embodiment, substrate 102 has a first surface 108 and a second surface 110 opposed to and parallel with the first surface 108 across a thickness 112 of the substrate 102. The substrate 102 also is defined by one or more substrate edges 104, 106. For example, in an embodiment that includes a rectangular substrate 102, the substrate 102 includes a first substrate edge 104 and a second substrate edge 106 opposed to and parallel with the first substrate edge 104 across a width 160 of the first surface 108. Substrate 102 also may include a third substrate edge 208 (FIG. 2) perpendicular to the first and second substrate edges 104, 106, and a fourth substrate edge 210 opposed to and parallel with the third substrate edge 208 across the first surface 108 (FIG. 2). A primary axis 170 is defined herein in a direction perpendicular to the first and second substrate edges 104, 106 and parallel with the first surface and second surfaces 108, 110.

According to an embodiment, substrate 102 includes one or more first luminescent "taggants" (e.g., substrate taggant 130), which are evenly or unevenly dispersed (e.g., integrated) within the material(s) comprising substrate 102, or within one or more layers of the substrate material(s) (e.g., when the substrate is a composite substrate). For example, the substrate taggant(s) 130 may be in the form of particles, which are mixed with other materials during formation of the substrate 102. When substrate taggant 130 is in a particle form, the particles may have particle sizes in a range from 1 micron to 20 microns, in an embodiment, although the particles may be smaller or larger than the above-given range, as well. In an alternate embodiment (not shown), the substrate taggant(s) may be included in a composition (e.g., an ink or other carrier) that is applied (e.g., printed, coated, sprayed or otherwise adhered or bonded) to a surface (e.g., surface 108 and/or 110) of the substrate 102. According to an embodiment, the substrate taggant(s) are included in the substrate materials or the substrate-applied composition in a range of about 0.02 to 0.4 wt %, although the substrate taggant(s) may be included in lower or higher percentages, as well.

As used herein, the term "taggant" means a material that includes one or more components that emit optical energy when excited by another targeted optical radiation. For example, a taggant may include one or more organic or inorganic luminescent types of compounds, including pigments, dyes, complex and/or chelate compositions, luminophores, and phosphors (referred to collectively herein as "luminescent materials" or "luminescent compounds"). In embodiments of taggants discussed herein, the presence of the one or more luminescent materials is detectable, upon exposure to appropriate excitation energy, by the human eye and/or using electronic equipment (e.g., authentication system 400, FIG. 4). The wavelength(s) of excitation energy appropriate to "excite" a particular taggant (i.e., to place an emitting ion of the taggant into an energy state at which it may produce detectable emissions) depend on the particular ion(s) within the taggant that function as the absorber(s). For example, some absorbing ions (e.g., chromium and other ions) may have an excitation range that covers the bulk of the visible spectrum, while other absorbing ions (e.g., neodymium and other ions) may have one or multiple distinct excitation ranges in the visible spectrum and/or in the near infrared (NIR) range. The selected wavelength and intensity of the excitation energy that is provided in conjunction with any particular detection system may depend on one or more factors (e.g., eye safety, thermal management, taggant material quantity, detector efficiency, cost, and so on). Generally, various engineering and other tradeoffs are considered in specifying the characteristics of excitation energy.

Once appropriately excited, the taggants may emit visible and/or infrared radiation in a range from about 400 to about 2400 nanometers (nm). As will be described in more detail later, a luminescent material incorporated into a luminescent taggant includes at least one emitting ion and optionally one or more sensitizing ions substituted into a host material. When such a luminescent material is exposed to excitation energy having an appropriate wavelength, the excitation energy may be absorbed directly by the emitting ions, and/or optionally by one or more sensitizing ions and/or by the host material with a subsequent transfer of the energy to the emitting ions. In whichever manner the excitation energy is absorbed, the emitting ions of the luminescent material produce emissions having unique characteristics (e.g., a unique spectral signature, a measurable decay time constant, and so on). More particularly, after being subjected to appropriate excitation energy, a luminescent material emits detectable radiation at one or more wavelengths within the visible and/or infrared portions of the electromagnetic spectrum.

Many luminescent materials produce concentrated emissions within one or more "emission bands" of the electromagnetic spectrum, where an "emission band" is defined herein to mean a continuous range of wavelengths within which concentrated, non-negligible (e.g., detectable) emissions occur from one or more emitting ions of the luminescent material. For any particular emitting ion, an "emission band" is bounded by a lower wavelength below which emissions are negligible for that ion, and an upper wavelength above which emissions are negligible for that ion. For example, erbium ions may emit radiation in emission bands centered at multiple wavelengths, including relatively strong emissions in emission bands centered at about 980 nm and about 1550 nm.

An embodiment of article 100 includes one or more extrinsic features 120 positioned proximate the first surface 108 of substrate 102. In addition, article 100 optionally may include one or more extrinsic features 122 positioned proximate the second surface 110. Although only one extrinsic feature 120, 122 is shown to be proximate each surface 108, 110, it is to be understood that more than one extrinsic feature may be proximate either or both surfaces 108, 110.

As used herein, the term "proximate a surface" (e.g., of substrate 102), means applied to the surface, embedded in the substrate so as to have emissions from the extrinsic feature that are detectable at the surface, or included as a feature that defines a portion of the surface. For example, an extrinsic feature that is "applied" to a surface may include a feature that is printed on, coated on, sprayed on, or otherwise adhered or bonded to a portion of the surface, such as extrinsic features 120, 122. Such an extrinsic feature may be applied to 100% of the portion of the surface at which it is located, or may be applied in a pattern that covers less than 100% of the portion of the surface at which it is located (e.g., from 10% to 30% or more). Regardless of the method of application employed, and as described in more detail later, the extrinsic features 120, 122 and any materials used in conjunction with the application method (e.g., adhesives, bonding materials, and so on) should not entirely mask, absorb, or otherwise attenuate excitation energy intended to excite substrate taggant 130 or substrate emissions that are produced as a result of providing the excitation energy to the substrate taggant 130. In contrast, an extrinsic feature that is "embedded" in the substrate may include one or more rigid or flexible materials in which or onto which a luminescent material is included. For example, an embedded extrinsic feature (not illustrated) may be configured in the form of a discrete, rigid or flexible substrate, a security thread, or another type of structure. An extrinsic feature that is included as a feature that "defines a portion of the surface" includes a feature having a top surface that is co-planar with the top surface (e.g., surface 108) of the substrate. The feature may extend partially through the substrate material or all the way through the substrate material. In the latter case, the extrinsic feature may have a bottom surface that is co-planar with the bottom surface (e.g., bottom surface 110) of the substrate. For purposes of example only, the description herein discusses features that are printed on a surface 108, 110 of a substrate 102. However, as indicated above, this example embodiment is not meant to limit the embodiments only to printed or otherwise surface-applied features.

Extrinsic features 120, 122 may be, for example, printed features or features that include one or more rigid or flexible materials. For example, extrinsic features 120, 122 may comprise a composition (e.g., an ink, pigment, coating, or paint) that includes a luminescent material as previously described. Alternatively, the surface-applied extrinsic feature 120 may comprise one or more rigid or flexible materials into which or onto which a luminescent material is included, where the substrate is then adhered, bonded or otherwise attached to a surface of the article substrate 102. According to various embodiments, surface-applied extrinsic feature 120 may have a thickness of about one micron or more, and surface-applied extrinsic feature 120 may have a width and length that is less than or equal to the width and length of the substrate 102.

According to an embodiment, extrinsic features 120, 122 include one or more second luminescent taggants (e.g., extrinsic feature taggant 132), which are evenly or unevenly dispersed (e.g., integrated) within the material(s) comprising extrinsic features 120, 122. For example, the extrinsic feature taggant(s) 132 may be in the form of particles, which are mixed with other materials during formation of the material that comprises the extrinsic features 120, 122. The extrinsic feature taggant 132 may be integrated within extrinsic feature 120, 122, for example, by mixing particles of the extrinsic feature taggant 132 into a base material (e.g., ink, and so on) for the extrinsic feature 120, 122. When extrinsic feature taggant 132 is in a particle form, the particles may have particle sizes in a range from 1 micron to 20 microns, in an embodiment, although the particles may be smaller or larger than the above-given range, as well. According to an embodiment, the extrinsic feature taggant(s) are included in the extrinsic feature materials in a range of about 0.2 to 30 wt %, although the extrinsic feature taggant(s) may be included in lower or higher percentages, as well.

Extrinsic features 120, 122 are proximate only a portion of each of surfaces 108, 110. In other words, at least a portion of surface 108 and/or surface 110 is devoid (or free) of any extrinsic feature 120, 122. A portion of a surface 108, 110 at which no extrinsic feature is present is referred to herein as a "substrate-only region" of the article. For example, regions 162, 166, 182, and 186 correspond to substrate-only regions of article 100. Conversely, a portion of a surface 108, 110 at which an extrinsic feature 120, 122 is present is referred to herein as an "extrinsic feature region" of the article. For example, regions 164 and 184 correspond to extrinsic feature regions of article 100.

In an alternate embodiment (not illustrated), an extrinsic feature taggant 132 may be included in an outer layer of a composite substrate (e.g., in an outer paper or plastic layer of the substrate). In such an embodiment, a gap in the outer layer that extends across an entire width of the substrate (e.g., in a direction perpendicular to primary axis 170) enables emissions from only the substrate taggant 130 to be detectable above the gap. Accordingly, the portion of the substrate that includes the gap would correspond to a "substrate-only region," and all other portions would correspond to "extrinsic feature regions."

According to an embodiment, the substrate taggant 130 produces emissions (referred to herein as "substrate emissions") in at least one emission band (referred to herein as "substrate emission band") when a portion of the substrate 102 that includes the substrate taggant 130 is exposed to excitation energy of an appropriate wavelength (referred to herein as "substrate excitation energy"). In addition, the extrinsic feature taggant 132 produces emissions (referred to herein as "extrinsic feature emissions") in at least one emission band (referred to herein as "extrinsic feature emission band") when an extrinsic feature 120, 122 that includes the extrinsic feature taggant 132 is exposed to excitation energy of an appropriate wavelength (referred to herein as "extrinsic feature excitation energy"). For example, when appropriate excitation energy is provided in substrate-only regions 162, 166, 182, 186 of article 100, substrate taggant 130 may produce substrate emissions in at least one substrate emission band.

Extrinsic features 120, 122 are configured in a manner that extrinsic features 120, 122 do not entirely mask, absorb, or otherwise attenuate excitation energy at the wavelength appropriate for exciting substrate taggant 130. In addition, extrinsic features 120, 122 are configured in a manner that extrinsic features 120, 122 do not entirely mask, absorb, or otherwise attenuate substrate emissions that are produced as a result of providing the appropriate excitation energy to the substrate taggant 130. Accordingly, in extrinsic feature regions 164, 184 of article 100, excitation energy may be provided to both the authentication taggant 132 and the underlying substrate taggant 130, and emissions above the surfaces 108, 110 of substrate 102 may be observable from both the authentication taggant 132 and the substrate taggant 130.

According to an embodiment, the substrate emission band and the extrinsic feature emission band at least partially overlap each other in an overlapping emission band (also referred to herein as a "confounded emission band"). Accordingly, in extrinsic feature regions 164, 184, the substrate emissions and the extrinsic feature emissions combine in the overlapping emission band to produce confounded emissions. As used herein, the term "confounded emissions" means a combination of emissions emanating from at least two taggants within in an overlapping emission band, where the confounded emissions have emission characteristics that are distinguishable from (i.e., different from) the emission characteristics of either or both of the taggants taken separately. As used herein, emission characteristics that are "distinguishable from" or "different from" each other are perceptibly different (as perceived by human or machine) in some measurable property of the emissions. For example, emission characteristics may be distinguishable from each other in emission intensity (or integrated intensity), temporal characteristics (e.g., emission decay time constant, emission rise time constant), branching ratio (e.g., ratio of integrated intensity in multiple bands), energy transfer to and emissions from another ion in another band, or a combination of such emission characteristics. For example, emission properties that are "perceptibly" different from each other are different by at least 5%, in an embodiment. In another embodiment, emission properties that are "perceptibly" different from each other are different by at least 10%, in an embodiment. In still another embodiment, emission properties that are "perceptibly" different from each other are different by at least 50%, in an embodiment. In still another embodiment, emission properties that are "perceptibly" different from each other are different by at least 100%, in an embodiment. The capabilities of a detection system, the degree of process control in generating taggants and articles, the resilience of articles and their features to wear and damage, and other factors may determine the range of percentages that are considered to be "perceptibly" different.

For example, when an extrinsic feature region 164, 184 of article 100 is exposed to excitation energy that is sufficient to produce emissions from both the substrate taggant 130 and the extrinsic feature taggant 132, substrate emissions from the substrate taggant 130 and extrinsic feature emissions from the extrinsic feature taggant 132 emanate from the exposed surface (e.g., from surface 108 or 110). As explained previously, the extrinsic feature emissions and the substrate emissions occur in an extrinsic feature emission band and a substrate emission band which at least partially overlap each other. Accordingly, confounded emissions that include components from the extrinsic feature emissions and the substrate emissions are produced in the extrinsic feature region 164, 184 within the overlapping emission band. The confounded emissions have emission characteristics that are distinguishable from the substrate emissions from substrate taggant 130 and from the extrinsic feature emissions from extrinsic feature taggant 132, taken separately. Accordingly, substrate emissions resulting from excitation of the substrate taggant 130 in a substrate-only region 162, 166, 182, 186 are distinguishable from confounded emissions in an extrinsic feature region 164, 184, even though the substrate and confounded emissions may occur within an overlapping emission band. As will be explained in more detail later, using an appropriately configured authentication system (e.g., authentication system 400, FIG. 4), emissions emanating from at least one substrate-only region 162, 164, 182, 184 and emissions emanating from at least one extrinsic feature region 164, 184 may be detected within a detection channel that corresponds to the overlapping emission band. Those emissions may be analyzed to determine whether the emissions have distinguishable emission characteristics from each other (e.g., characteristics corresponding to substrate emissions and confounded emissions, respectively).

According to an embodiment, the substrate taggant 130 and the extrinsic feature taggant 132 are selected so that, at least within the confounded emission band, the substrate emissions and the combined substrate/extrinsic feature emissions have perceptibly different emission characteristics from each other (even though some of their emissions occur in overlapping emission bands). For example, within the confounded emission band, the substrate taggant 130 may have a first emission intensity (or integrated emission intensity), and the extrinsic feature taggant 132 may have a second emission intensity (or integrated emission intensity), which may or may not be different from the first emission intensity. In addition or alternatively, the substrate taggant 130 may have a first decay time constant, and the extrinsic feature taggant 132 may have a second decay time constant, which may or may not be different from the first decay time constant. Either way, when the emissions from the substrate taggant 130 and the extrinsic feature taggant 132 combine, the combined emissions (i.e., the confounded emissions) are perceptibly different from the substrate emissions taken alone. For example, the confounded emissions may have an emission intensity (or integrated emission intensity) that is perceptibly greater than the emission intensity of the substrate-only emissions. More particularly, emissions within the confounded emission band emanating from an extrinsic feature region (e.g., region 164) may have a perceptibly higher emission intensity (or integrated intensity) than emissions within the confounded emission band emanating from a substrate-only region (e.g., region 162). As another example, the confounded emissions may have a decay time constant that is perceptibly greater or less than the decay time constant of the substrate-only emissions. Other emission characteristics may be different, as well.

Different emission characteristics within the confounded emission band for substrate-only and extrinsic feature regions may be achieved in any of a number of ways, in various embodiments. For example, substrate taggant 130 may include a first emitting ion that produces substrate emissions within the confounded emission band, and extrinsic feature taggant 132 may include a second (different) emitting ion that produces extrinsic feature emissions within the confounded emission band. In alternate embodiments, substrate taggant 130 and extrinsic feature taggant 132 may include the same emitting ion, although the taggants 130, 132 differ in other ways that cause the taggants 130, 132 to produce emissions with different characteristics. For example, the emitting ion may be included in the substrate taggant 130 at a first doping density, and the emitting ion may be included in the extrinsic feature taggant 132 at a second doping density that is different from (e.g., higher than) the first doping density. The difference in the first and second doping densities may be relatively small (e.g., as low as 5%) or large (e.g., 100% or greater), depending on the selected ions and host material. Regardless of the difference in the first and second doping density, the difference should be sufficient to produce the perceptibly different emission characteristics.

In another embodiment in which the emitting ion is the same in the substrate and extrinsic feature taggants 130, 132, the substrate taggant 130 may include a first host material with which the emitting ion is incorporated, and the extrinsic feature taggant 132 may include a second host material with which the emitting ion is incorporated, where the first and second host materials are different from each other so as to produce different emission characteristics from the same emitting ion. In such an embodiment, for example, the emitting ion may be substituted into a first host lattice to produce the substrate taggant 130, and the emitting ion may be substituted into a second, different host lattice to produce the extrinsic feature taggant 132. In still another embodiment, the emitting ions and host materials may be the same in both the substrate and extrinsic feature taggants 130, 132. However, even though the taggants 130, 132 are substantially the same (including having the same spectral and temporal signatures), the increased quantity of taggants in the extrinsic feature regions (e.g., region 164) may be sufficient to produce confounded emissions that are perceptibly different from the emissions from the substrate taggant 130 alone.

According to an embodiment, as an additional authentication criteria, article 100 may include a third luminescent taggant 134 which, when exposed to appropriate excitation energy, produces emissions within at least one emission band that does not overlap the confounded emission band associated with the substrate emissions and the extrinsic feature emissions. Alternatively, as will be explained in more detail later, either the substrate taggant or the extrinsic feature taggant may produce emissions having such non-overlapping characteristics. In an embodiment in which a third luminescent taggant 134 is included, the third luminescent taggant 134 includes at least one emitting ion associated with the non-overlapping emissions, and this emitting ion may be different from the emitting ion(s) associated with the substrate and extrinsic feature emissions. According to an embodiment, the confounded emission band associated with the substrate and extrinsic feature taggants 130, 132 and the non-overlapping emission associated with the third taggant 134 are sufficiently separated, in wavelength, so that different types or classes of photodetectors are used to measure the emission properties of the associated luminescent materials. In an alternate embodiment, the confounded and non-overlapping emission bands may be sufficiently close to each other to enable a same type or class of photodetector to be used to measure emissions within the different bands.

For the purpose of distinguishing the third taggant 134 and its associated emissions from the substrate taggant 130, the extrinsic feature taggant 132, and their associated emissions, the third taggant 134 will be referred to herein as a "supplemental taggant" 134, and its emissions will be referred to as "supplemental emissions." Similarly, excitation energy having a wavelength appropriate to induce the supplemental emissions is referred to herein as "supplemental taggant excitation energy." The supplemental taggant excitation energy may be substantially the same as or different from the substrate and/or extrinsic feature excitation energy (energies), in various embodiments. Finally, a non-overlapping emission band within which emissions from the supplemental taggant 134 may be produced is referred to herein as a "supplemental emission band." It is to be understood that, in addition to producing emissions in a supplemental emission band, a supplemental taggant 134 may produce emissions that overlap the extrinsic feature and/or substrate emission bands, as well.

The supplemental taggant 134 may be in the form of particles, which may have particle sizes in a range from 1 micron to 20 microns, in an embodiment, although the particles may be smaller or larger than the above-given range, as well. In an embodiment, the supplemental taggant 134 may be evenly or unevenly dispersed within the material(s) comprising a supplemental feature 124, 126 (e.g., a printed feature, embedded feature, security thread, and so on) that is extrinsic from the extrinsic feature 120, 122, as shown in FIGS. 1 and 2. Although only supplemental feature 124, 126 is shown to be proximate each surface 108, 110 in FIG. 1, it is to be understood that more than one supplemental feature may be proximate either or both surfaces 108, 110.

Each supplemental feature 124, 126 may be proximate a portion of a substrate surface 108, 110 that is different from the portion of the substrate surface 108, 110 at which the extrinsic feature 120, 122 is proximate. For example, as shown in FIGS. 1 and 2, supplemental features 124, 126 are spatially distinct from extrinsic features 120, 122 in a direction along the primary axis 170. In such an embodiment, as shown in FIG. 2, an authentication system may attempt to excite and detect both the extrinsic feature 120 and the supplemental feature 124 along a first pre-defined track 220. Alternatively, a supplemental feature 202 may be spatially distinct from extrinsic feature 120 in a direction perpendicular to the primary axis 170. In such an embodiment, an authentication system may attempt to excite and detect the extrinsic feature 120 along the first pre-defined track 220, and the authentication system may attempt to excite and detect the supplemental feature 202 along a second pre-defined track 222 that is parallel with but spatially separated from the first pre-defined track 220. In still another embodiment, a supplemental feature 204 may be spatially distinct from extrinsic feature 120 in both the direction of the primary axis 170 and in a direction perpendicular to the primary axis 170.

In an alternate embodiment, a supplemental feature may be proximate a same portion of a substrate surface 108, 110 as an extrinsic feature 120, 122. For example, a supplemental feature may be applied over or under an extrinsic feature, or a supplemental feature may be applied in a manner in which it is interleaved with an extrinsic feature (including stripes, concentric shapes, and so on).

In another alternate embodiment, the supplemental taggant 134 may be evenly or unevenly dispersed within the material(s) comprising the extrinsic feature 120, 122. In such an embodiment, the extrinsic feature taggant 132 and the supplemental taggant 134 may actually be the same taggant (referred to herein as a "multiple band feature taggant"). For example, a multiple band feature taggant may include a host material with both the emitting ion(s) associated with the extrinsic feature emissions and the emitting ion(s) associated with the supplemental emissions. Alternatively, the host material may include an emitting ion that contributes to both the extrinsic feature emissions and the supplemental emissions. In another embodiment, for example, the emitting ions associated with the extrinsic feature emissions and the supplemental emissions may be substituted into different host materials, although both materials are included in the multiple band feature taggant.

In yet another alternate embodiment, the supplemental taggant 134 may be evenly or unevenly dispersed within the material(s) comprising the substrate 102. In such an embodiment, the substrate taggant 130 and the supplemental taggant 134 may actually be the same taggant (referred to herein as a "multiple band substrate taggant"). For example, a single multiple band substrate taggant may include both the emitting ion(s) associated with the substrate emissions and the emitting ion(s) associated with the supplemental emissions. In an embodiment, for example, the emitting ions associated with the substrate emissions and the supplemental emissions may be substituted into a same host material. In another embodiment, for example, the emitting ions associated with the substrate emissions and the supplemental emissions may be substituted into different host materials, although both materials are included in the multiple band substrate taggant.

According to an embodiment, the substrate excitation energy and the extrinsic feature excitation energy may be substantially the same (e.g., at substantially the same wavelength). In such an embodiment, a single excitation energy generator (e.g., one of generators 404, FIG. 4) may be used to provide the substrate and extrinsic feature excitation energy. Alternatively, different excitation energy generators may be used, where each excitation energy generator produces the same excitation energy, but the energy is directed to spatially separated physical tracks (e.g., tracks 220, 222, FIG. 2). In an alternate embodiment, the substrate excitation energy and the extrinsic feature excitation energy may be different from each other (e.g., at different wavelengths). In such an embodiment, multiple excitation energy generators (e.g., generators 404, FIG. 4) may be used to provide the substrate and extrinsic feature excitation energy (e.g., along the same or spatially separated tracks).

According to an embodiment, the supplemental taggant excitation energy may be substantially the same as the substrate and/or extrinsic feature excitation energy. In another embodiment, the supplemental taggant excitation energy may be different from both the substrate excitation energy and the extrinsic feature excitation energy.

As yet another authentication criteria and/or for use in determining an article orientation (e.g., for sorting or other purposes), the authentication system may determine the location(s), on the surface 108, 110 of the substrate 102, where confounded emissions are detected. An authentication system may receive an article being authenticated (e.g., article 102) in any of multiple possible orientations. For example, an article may be provided to an authentication system with its primary axis (e.g., primary axis 170) in a controllable and known direction. However, the article may not be provided in a known orientation, with respect to the authentication system. For example, in the embodiments depicted in FIGS. 1 and 2, article 100 may be presented to an authentication system in any of four orientations. For example, article 100 may be presented with surface 108 facing up or down. In addition, article 100 may be presented with either substrate edge 104 or 106 being the "incident" edge (i.e., the edge that is presented first to the authentication system, or the edge at which the authentication system initiates its excitation and detection processes).

A single-sided authentication system attempts to detect extrinsic features on only one side of an article. Accordingly, if such a system is to be capable of determining an orientation of the article, the features of the article should be configured to enable such a determination. According to an embodiment, extrinsic features 120, 122 are proximate both surfaces 108, 110 of the article 100 in order to ensure that a single-sided authentication system can observe at least one extrinsic feature 120, 122 during a single pass through the system. In addition, the location of extrinsic features 120, 122 enables a definitive determination to be made regarding article orientation using a single-sided authentication system. More particularly, the location of extrinsic features 120, 122 enables a determination of which surface 108 or 110 is being analyzed, and indicates which substrate edge 104 or 106 is the incident edge.

A double-sided authentication system may attempt to detect extrinsic features on both sides of an article. Accordingly, a double-sided authentication system may at least partially determine an orientation of an article (e.g., whether the article is face up or face down), even in an embodiment of an article that includes an extrinsic feature (e.g., extrinsic feature 120) proximate only a single surface (e.g., surface 108). However, if such a system is to be capable of definitively determining the orientation of the article (e.g., whether substrate edge 104 is to the left or right), the features of the article should be configured to enable such a determination. Once again, according to an embodiment, the location of even a single extrinsic feature 120 enables a definitive determination to be made regarding article orientation using a double-sided authentication system. More particularly, the location of one or more extrinsic features 120, 122 enables a determination of which surface 108 or 110 is face up, and indicates which substrate edge 104 or 106 is the incident edge. Because the orientation analysis for a double-sided authentication system may be simpler than the orientation analysis for a single-sided authentication system, an orientation analysis for the single-sided authentication system is discussed below, to fully illustrate the various embodiments. Those of skill in the art will understand how to simplify the analysis to apply to a double-sided authentication system.

As mentioned above, an authentication system provides excitation energy to an article surface along a pre-defined excitation track (e.g., tracks 220, 222, FIG. 2) that extends from an incident edge to a "trailing" edge (i.e., the edge that is presented last to the authentication system, or the edge at which the authentication system terminates its excitation and detection processes). In addition, authentication system attempts to detect emissions resulting from the excitation energy along a pre-defined detection track (e.g., tracks 220, 222, FIG. 2), which is collinear with the pre-defined excitation track (although perhaps narrower). Accordingly, for a double-sided article (e.g., article 100), depending on the orientation in which the article 100 is presented to the authentication system, the excitation and detection activities may traverse a pre-defined excitation track by either: 1) proceeding across a first surface 108 of the article 100 starting from incident substrate edge 104 and moving toward trailing substrate edge 106, as indicated by arrow 190; 2) proceeding across a first surface 108 of the article 100 starting from incident substrate edge 106 and moving toward trailing substrate edge 104, as indicated by arrow 192; 3) proceeding across a second surface 110 of the article 100 starting from incident substrate edge 104 and moving toward trailing substrate edge 106, as indicated by arrow 194; or 4) proceeding across a second surface 110 of the article 100 starting from incident substrate edge 104 and moving toward trailing substrate edge 106, as indicated by arrow 190.

According to an embodiment, in an authentic article, extrinsic feature 120 proximate a first side 108 of substrate 102 has a first feature edge 140 that is a known first distance 163 from first substrate edge 104. In addition, the extrinsic feature 120 has a second feature edge 142 that is a known second distance 167 from the second substrate edge 106 (or a known distance from the first substrate edge 104). The first distance 163 and the second distance 167 are different from each other, in an embodiment, although they may be substantially the same, in another embodiment. According to a further embodiment, extrinsic feature 122 proximate a second side 110 of substrate 102 has a third feature edge 144 that is a known third distance 183 from first substrate edge 104. In addition, the extrinsic feature 122 has a fourth feature edge 146 that is a known fourth distance 187 from the second substrate edge 106 (or a known distance from the first substrate edge 104). The first distance 163, the second distance 167, the third distance 183, and the fourth distance 187 all are different from each other, in an embodiment, although some or all of the first, second, third, and fourth distances 163, 167, 183, 187 may be substantially the same, in other embodiments.

According to an embodiment, an authentication system is capable of determining the location of an extrinsic feature (e.g., either extrinsic feature 120 or 122), with respect to an incident edge (e.g., either substrate edge 104 or 106) by determining where confounded emissions emanating from a surface (e.g., surface 108 or 110) are detected. For an authentic article, the location determination indicates whether an extrinsic feature (e.g., either feature 120 or 122) is located a first, second, third or fourth distance 163, 167, 183, 187 from the incident substrate edge (either substrate edge 104 or 106). For example, when the authentication system determines that an extrinsic feature is located the first distance 163 from an incident edge (i.e., edge 104), the authentication system determines that the article is in the orientation shown in FIG. 1. Similarly, when the authentication system determines that an extrinsic feature is located either the second, third, or fourth distances 167, 183, 187 from an incident edge (i.e., either edge 104 or 106), the authentication system determines that the article is in one of the other three possible orientations.

In addition to detecting a location of an extrinsic feature for the purpose of determining an orientation of an article, the authentication system also may determine whether the detected extrinsic feature is in an expected location, in order to provide an additional measure of article authenticity. More particularly, when an extrinsic feature is detected, but it is not located the first, second, third or fourth distances 163, 167, 183, 187 from an incident edge, the authentication system may determine that the article is not authentic.

Although the above description discusses embodiments in which article orientation is determined based on a determined location of an extrinsic feature, article orientation alternatively may be determined based on a determined location of a supplemental feature (e.g., supplemental features 124, 126), as well. In addition, a determination of the location of a supplemental feature may be used as an additional measure of article authenticity.

The various relative dimensions of the substrate 102, extrinsic features 120, 122, supplemental features 124, 126, and particles 130, 132, 134, may not be to scale in FIG. 1. Although article 100 is illustrated to include surface-applied extrinsic and supplemental features 120, 122, 124, 126, another article may include one or a combination of embedded extrinsic and supplemental features, and surface-applied extrinsic and supplemental features. Finally, although only a single extrinsic feature 120, 122 and a single supplemental feature 124, 126 are shown on each surface 108, 110 of substrate 102 in FIG. 1, an article may include more than one extrinsic feature 120, 122 and/or supplemental feature 124, 126 on either or both surface 108, 110 of substrate 102.

Example luminescent materials will now be described, which may be included as luminescent materials in the taggants employed in the various embodiments discussed herein. According to an embodiment, a luminescent material suitable for use in a luminescent taggant includes a host material (e.g., a host crystal lattice, glass, and so on) and one or more emitting ions (i.e., emitting ion(s) mixed or substituted into the host material). The luminescent material also may include other materials (e.g., one or more sensitizing ions), as well, although such other materials are discussed herein in detail.

An emitting ion within a luminescent material may be characterized by detectable emissions in a single emission band, or in multiple emission bands. The emission intensity in any particular emission band may be directly related to the percentage of the emitting ion in the host material (e.g., the doping or substitution percentage, in the case of a host crystal lattice material). More specifically, the emission intensity may be relatively low for relatively low percentages of the emitting ion in the host material, and may be relatively high for relatively high percentages of the emitting ion in the host material.

There are at least three mechanisms for an emitting ion to receive energy for subsequent radiation. For example, the emitting ion may be capable of directly absorbing excitation energy, and the emitting ion may thereafter radiate at least some of the absorbed energy (typically at a different and longer wavelength from the excitation energy). Alternatively, the host material or an ion thereof (e.g., a vanadate ion) may be capable of absorbing excitation energy directly, and transferring energy to the emitting ion. In other situations, the host material may contain one or more "host material ions" that may be substituted by emitting ions, and optionally one or more sensitizing ions that may absorb excitation energy and transfer the resulting energy to the emitting ions. Host material absorption may be useful, in some cases, although host material absorption is not particularly useful in a majority of cases. More typically, a transition metal ion (e.g., chromium) or a rare earth metal ion (e.g., erbium) is used as a sensitizing ion. These elements also may act as emitting ions, or they also may transfer the energy to other ions (e.g., emitting ions), which then radiate the transferred energy. Virtually all host materials may act as absorbers in the ultraviolet range because the exciting photon energy is very high in this range. However, this phenomenon may not yield any desired emission at all from incorporated desired ions.

The ions that may be replaced are ions within the host material that may be substituted by one or more sensitizing ions, if included, and one or more emitting ions, up to and including 100% substitution. 100% substitution is rare since most emitting ions are concentration quenched well below a 100% substitution level. However, there are a few notable exceptions in which particular ions and host lattice combinations that allow for greater substitutions since the physical separation of the emitting ions in the host lattice is sufficiently far apart so that the interaction term is significantly reduced.

The emitting ions may be substituted at very low substitution percentages (e.g., doped at less than 1%), medium substitution percentages (e.g., from 1% to 20%), or high substitution percentages (e.g., from 20% to 100%). For example, neodymium (Nd) may be substituted at relatively low percentages up to 1.5%, holmium (Ho) and ytterbium (Yb) may be substituted at medium percentages up to 20%, and erbium (Er) may be substituted at relatively high percentages up to 60%, although these and other ions may be substituted at different percentages, as well. As used herein, the term "substituted" means substituted at any percentage, including low, medium, and high substitution percentages. The amount of each ion substituted into a host material is generally described in terms of atomic percent, where the number of ions of the host material that may be replaced by sensitizing and/or emitting ions is equal to 100%. An ion of a host material that allows for replacement with sensitizing and/or emitting ions may typically have similar size, similar loading, and similar coordination preference as the ions it will be replaced with. As various positions within a host material may occur, the ions on each of these positions will be accounted for 100 atomic percent.

The host material comprises a material into which emitting ions and optionally sensitizing agents are incorporated (e.g., mixed or substituted). In an embodiment, the host material may be in the form of a crystal lattice into which different chemical constituents may substitute at various positions within the lattice. The host material should be selected to ensure that the emitting ion will produce observable emissions within at least one emission band, where the emissions are suitable for analysis using embodiments of authentication equipment and methods described in detail below. In various embodiments, the host material includes a material selected from a group consisting of a glass, an oxide, a fluoride, an oxysulfide, a halide, a borate, a silicate, a gallate, a phosphate, a vanadate, an oxyhalide, an aluminate, a molybdate, a tungstate, a garnet, a niobate, a nitride, an oxynitride, and mixtures thereof, although other host materials may be used, as well. For example, the host material may include yttrium (Y) oxysulfide ($Y_2O_2S$ or YOS), a yttrium aluminum garnet (YAG), yttrium gallium garnet (YGG), a gadolinium (Gd) gallium garnet (GGG), gadolinium oxysulfide ($Gd_2O_2S$ or GOS), or other materials. According to further embodiments, the substrate emission band, the extrinsic feature emission band, and the supplemental emission band each independently correspond to an emission band of at least one emitting ion after incorporation (e.g., substitution) into at least one host material selected from a group of materials consisting of the above-listed materials or their combinations.

A suitable emitting ion includes an ion that has one or more, relatively strong emissions within one or more emission bands. According to various embodiments, the emitting ion includes an ion of an element selected from a group consisting of chromium (Cr), manganese (Mn), iron (Fe), cobalt (Co), copper (Cu), silver (Ag), cerium (Ce), praseodymium (Pr), neodymium (Nd), samarium (Sm), europium (Eu), terbium (Tb), dysprosium (Dy), holmium (Ho), erbium (Er), thulium (Tm), and ytterbium (Yb). For example, the emitting ion may have +3 valences, in an embodiment, although the emitting ion may have different valences (e.g., +2 and/or +4), in other embodiments. According to various embodiments, the substrate emission band, the extrinsic feature emission band, and the supplemental emission band each independently correspond to an emission band of at least one ion of at least one element selected from a group of elements consisting of the above-listed elements or their combinations.

In various embodiments, the total concentration of emitting ions substituted into the host material is sufficient to cause the luminescent material to produce a detectable emission after being appropriately subjected to excitation energy. For example, the total concentration of emitting ions substituted in the host material may be in a range from about 0.05 atomic percent to about 99.995 atomic percent. However, the concentration of emitting ions that may be substituted while still producing the functionality of the luminescent material (e.g., the functionality of producing an emission upon exposure to excitation energy) depends on the type of ion that is being substituted. In other words, some ions may be substituted at relatively high percentages while still maintaining the functionality of the luminescent material, but the functionality may be defeated if other ions are substituted at the same, relatively high percentages.

In some cases, an emitting ion is excited via a direct absorption process, which includes providing excitation energy within the absorption band for the emitting ion. Alternatively, the host material or a sensitizing ion may function as a path to excite the emitting ion, as described previously. In the former case, the emission from the emitting ion decays rapidly from the absorption resonance level to a storage level. Generally, the absorption band is above the storage level, although this is not always the case, and the decay time from the absorption resonance level is very rapid compared to the decay time from the storage level. From the storage level, spontaneous photon emission may occur at a wavelength band determined by the storage level and a lower energy level.

As will be explained in more detail below, the characteristics of the emitted electromagnetic radiation from the emitting ions may be used to determine whether or not the luminescent material (e.g., the phosphor or other type of compound) corresponds to an "authenticating" luminescent material and, thus, an "authenticating" luminescent taggant. More particularly, after exposure to excitation energy, the emitting ion(s) within a luminescent material emit photons, and the intensities (or integrated intensities) of the emissions within one or more detection bands (or channels) may be observed. As will be described in more detail below, analysis of the emission intensities at multiple locations on an article facilitate a determination of whether an article is authentic.

Figure 3:
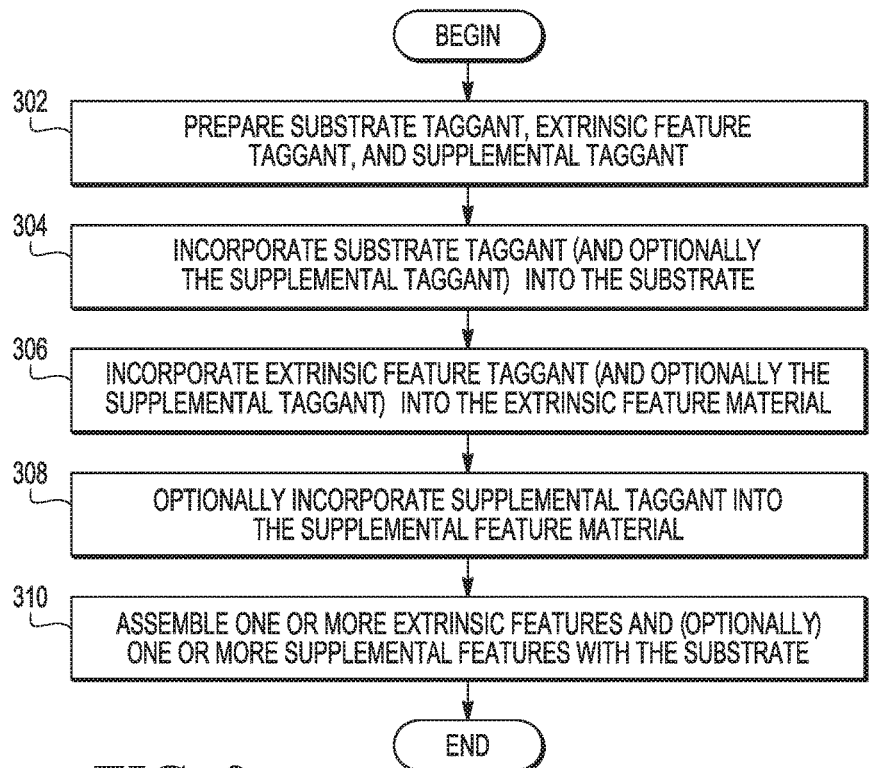
FIG. 3 is a flowchart of a method for producing an article, in accordance with an example embodiment.

FIG. 3 is a flowchart of a method for producing an article (e.g., article 100, FIG. 1), in accordance with an example embodiment. The method begins, in block 302, by preparing a substrate taggant, an extrinsic feature taggant, and optionally a supplemental taggant (e.g., substrate taggant 130, extrinsic feature taggant 132, and supplemental feature taggant 134, FIG. 1). Preparation of each taggant commences with procuring or producing a corresponding luminescent material, in an embodiment.

Generally, a luminescent material may be created using any of a number of conventional processes that are known to those of skill in the art. For example, creation of a phosphor compound includes preparing a combination of a phosphor host material (e.g., a host crystal lattice, glass, and so on) and one or more emitting ions (e.g., one or more of the aforementioned emitting ions) to form a preliminary phosphor compound. According to an embodiment, different preliminary phosphor compounds are prepared corresponding to each of the substrate taggant, the extrinsic feature taggant, and the supplemental taggant. As discussed previously, the substrate taggant and the extrinsic feature taggant may include the same or different emitting ions, and the same or different host materials. Either way, however, the emitting ions and the host materials should be selected so that an emitting ion in the substrate taggant is capable of producing emissions in a substrate emission band, and an emitting ion in the extrinsic feature taggant is capable of producing emissions in an extrinsic feature emission band that at least partially overlaps the substrate emission band. When a supplemental taggant also is employed, an emitting ion and a host material for the supplemental taggant should be selected so that the emitting ion is capable of producing emissions in a supplemental emission band that does not overlap the substrate or extrinsic feature emission bands. As discussed previously, the emitting ion(s) associated with the supplemental taggant may be included with a host material for either the substrate or the extrinsic feature, in some embodiments (e.g., when the supplemental taggant is the same as either the substrate taggant or the extrinsic feature taggant).

In some cases, formation of the preliminary phosphor compound may be achieved using solid state chemistry. For example, when the phosphor compound is an oxide phosphor, this may include combining correct proportions of various oxides with oxides of the emitting ion. These oxides are mixed and fired for a prescribed time. In other cases, solution chemistry techniques may be used, in which the various materials are dissolved, subsequently precipitated, and subsequently fired.

Depending on the particular process used to create the compound, other materials may be included in the combination of the host material and the emitting ion(s) in forming the preliminary phosphor compound. For example, various fluxing agents and other pre-cursors may be included within the preliminary phosphor compound.

Each preliminary phosphor compound is then post-processed, resulting in a luminescent material corresponding to each of the substrate taggant, the extrinsic feature taggant, and the supplemental taggant. For example, post-processing may include performing any one or more of the following processes to the preliminary phosphor compound: firing; annealing; suspension; precursor removal (e.g., to remove fluxing agents); milling; sedimentation; and sonication. Although the above discussion relates to preparation of a phosphor compound as a luminescent material in a taggant, the discussion is not meant to be limiting. Instead, as discussed previously, other luminescent materials also may be used in a substrate taggant, extrinsic feature taggant, and/or supplemental taggant.

In block 304, the substrate taggant (and optionally the supplemental taggant if it is not incorporated into an extrinsic feature or into a supplemental feature) is incorporated into the substrate. The substrate taggant may be incorporated into the substrate, for example, by mixing particles of the substrate taggant into a base material (e.g., paper pulp, plastic base resin, and so on) for the substrate, and/or by impregnating the substrate with a colloidal dispersion of particles of the substrate taggant. Impregnation may be performed, for example, by a printing, dripping, coating or spraying process.

In block 306, which also may be performed before or concurrently with block 304, the extrinsic feature taggant (and optionally the supplemental taggant if it is not incorporated into the substrate or into a supplemental feature) is incorporated into the extrinsic feature material. As discussed previously, an extrinsic feature may be a printed feature, an embedded feature, a security thread, and so on. For embedded features and security threads that include a rigid substrate, incorporation of the extrinsic feature taggant into the feature substrate may be performed in a similar manner to incorporation of the substrate taggant into the substrate, as discussed above. For a printed extrinsic feature, particles of the extrinsic feature taggant are mixed into a composition (e.g., an ink or other carrier), which may be applied to (e.g., printed on, coated on, sprayed on, or otherwise adherable to or bondable to) a surface (e.g., surface 108 and/or 110).

Block 308 is performed in an embodiment in which the supplemental taggant is included in a distinct feature of an article (e.g., supplemental feature 134, 126, FIG. 1). In block 308, which also may be performed before or concurrently with blocks 304 and 306, the supplemental taggant is incorporated into the supplemental feature material. As discussed previously, a supplemental feature may be a printed feature, an embedded feature, a security thread, and so on. For embedded features and security threads that include a rigid substrate, incorporation of the supplemental taggant into the feature substrate may be performed in a similar manner to incorporation of the substrate taggant into the substrate, as discussed above. For a surface-applied supplemental feature, particles of the supplemental taggant are mixed into a composition (e.g., an ink or other carrier), which may be applied to a surface (e.g., surface 108 and/or 110).

In block 310, the article is produced by assembling one or more extrinsic features (e.g., extrinsic features 120, 122, FIG. 1) and (optionally) one or more supplemental features (e.g., supplemental features 124, 126, FIG. 1) with the substrate (e.g., substrate 102, FIG. 1). For example, when the extrinsic features (and optionally the supplemental features) are surface-applied features, the composition corresponding to the extrinsic feature material may be printed onto one or more surfaces of the substrate in pre-determined locations. Conversely, when the extrinsic features (and optionally the supplemental features) are embedded features, the substrate corresponding to the embedded feature is integrated with the substrate material when the substrate material is in a malleable form (e.g., when the material is a slurry, molten, or non-cured form). An article corresponding to an embodiment (e.g., article 100, FIG. 1) is produced upon completion of the assembly of the substrate and the extrinsic feature(s) (and optionally the supplemental feature(s)).

Figure 4:
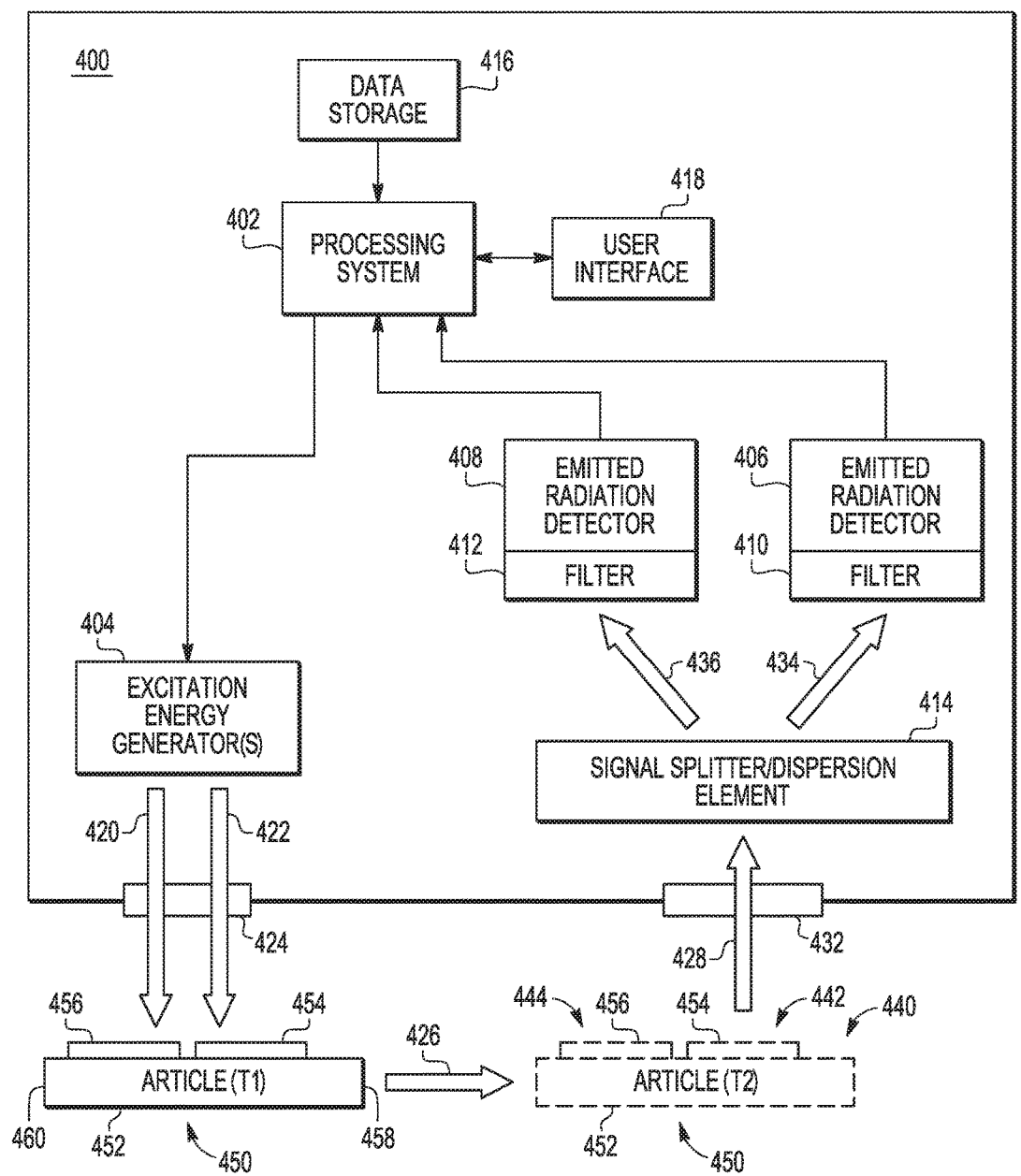
FIG. 4 is a system for authenticating an article, in accordance with an example embodiment.

FIG. 4 is a system 400 for authenticating an article 450, in accordance with an example embodiment. System 400 includes a processing system 402, one or more excitation energy generators 404, one or more emissions photodetectors ("detectors") 406, 408 with associated optical filters (filters) 410, 412, a signal splitter/dispersion element 414, data storage 416, and a user interface 418, according to an embodiment. Processing system 402 may include one or more processors and associated circuitry, which is configured to implement control and analysis processes (e.g., in the form of executable software algorithms) associated with authenticating an article (e.g., article 450).

Article 450 includes a substrate 452, an extrinsic feature 454, and a supplemental feature 456, as discussed previously. In an embodiment, article 450 is transported through the authentication system 400 in a processing direction 426, with an incident edge 458 of article 450 being presented to the system 400 first, and a trailing edge 460 of the article 450 being presented to the system 400 last. For example, at a first time (T1), article 450 is passed under an excitation window 424 of system 400, and at a second, subsequent time (T2), article 450 is passed under a detection window 432 of system 400. In an alternate embodiment, article 450 may be moved into a stationary position within the authentication system 400, and the excitation and detection windows 424, 432 may be moved over the stationary article 450.

Either way, according to an embodiment, processing system 402 is configured to provide control signals to an excitation energy generator 404, which cause excitation energy generator 404 to direct first excitation energy 420 toward article 450 along a pre-defined excitation track (e.g., track 220, FIG. 2) having a width corresponding to a width of the excitation window 424. Excitation energy generator(s) 404 may include, for example, one or more filtered LEDs (light emitting diodes), laser diodes, or other radiation sources. As the article 450 is moved under the excitation window 424 (or the excitation window 424 is moved over the article 450), emitting ions in the substrate and extrinsic feature taggants, receive energy for subsequent radiation (using one or more energy absorption and/or transfer mechanisms). As discussed previously, the excitation energy for the substrate and extrinsic feature taggants is the same (e.g., the same wavelength), although different excitation energy may be provided for the substrate and extrinsic feature taggants, in another embodiment.

In an embodiment in which a supplemental taggant also is analyzed, processing system 402 also is configured to provide control signals to the same or a different excitation energy generator 404, which cause the excitation energy generator 404 to direct second excitation energy 422 toward article 450 along the pre-defined excitation track. As the article 450 is moved under the excitation window 424 (or the excitation window 424 is moved over the article 450), emitting ions in the supplemental taggant (referred to as "supplemental ions"), receive energy for subsequent radiation (using one or more energy absorption and/or transfer mechanisms). In an embodiment, the excitation energy for the supplemental taggant is different from the excitation energy for the substrate and extrinsic feature taggants, although the excitation energy for all of the taggants may be the same, in another embodiment.

In the control signals, processing system 402 may specify the timing (e.g., start time, stop time, and/or duration) of the provision of excitation energy, and/or other parameters associated with the particular excitation energy to be generated (e.g., intensities and/or other parameters). Typically, the bandwidth of the excitation energy is pre-determined based on the excitation source that is included as part of the excitation energy generator 404 (e.g., the bandwidth of excitation energy produced by a selected light emitting diode or laser diode). The various timing and/or radiation generation parameters may be retrieved from data storage 416, for example. Excitation energy generator 404 may include, for example, one or more lasers, laser diodes, light-emitting diodes (LEDs), incandescent filaments, lamps, or other excitation sources.

In addition to controlling excitation energy generator 404, processing system 402 is configured to provide control inputs to emissions detectors 406, 408, which cause emissions detectors 406, 408 to attempt to detect emissions 428 emanating from various regions of article 450 in response to various emitting ions having absorbed (either directly or indirectly) at least some of the excitation energy 420, 422. For example, in a substrate-only region 440 of article 450 (e.g., region 162, FIG. 1), article 450 may produce emissions 428 corresponding to a substrate taggant (e.g., substrate taggant 130, FIG. 1). In an extrinsic feature region 442 of substrate 450 (e.g., region 164, FIG. 1), article 450 may produce confounded emissions 428 that include emission components from the substrate taggant and the extrinsic feature taggant (e.g., taggants 130, 132, FIG. 1). In addition, in an area 444 in which a supplemental taggant is present (e.g., in supplemental feature 456), article 450 may produce supplemental emissions 428.

According to an embodiment, the emissions 428 impinge upon the signal splitter/dispersion element 414, which separates the emissions 428 into beams 434, 436. One beam 434 includes light within a first band (e.g., a band that includes the overlapping emission band corresponding to the substrate, extrinsic feature, and confounded emissions), and the second beam 436 includes light within a second band that does not overlap and is separated from the first band (e.g., a band associated with the non-overlapping supplemental emissions). Signal splitter/dispersion element 414 directs the first beam 434 toward one of detectors 406, and directs the second beam 436 toward the other of detectors 408. According to an embodiment, signal splitter/dispersion element 414 is configured to pass the first beam 434 and to reflect the second beam 436. For example, signal splitter/dispersion element 414 may be an element selected from a group consisting of a polychromator, a prism, diffraction grating, a thin-film filter, an interference filter, a dichroic filter, a dichroic mirror, and a dichroic reflector. An advantage to such a signal splitter/dispersion element 414 is that it enables both detectors 406, 408 simultaneously to receive components of an emission that emanated from a same area of the article 450, thus maximizing correlation of the resulting intensity measurements.

Each emissions detector 406, 408 may include, for example, a spectral filter 410, 412, one or more electro-optical sensors, photomultiplier tubes, avalanche photodiodes, photodiodes, charge-coupled devices, charge-injection devices, photographic films, or other detection devices. In a particular embodiment, each emissions detector 406, 408 includes a spectral filter 410, 412 positioned between the signal splitter/dispersion element 414 and a photodetector. The spectral filters 410, 412 are configured to filter the beams 434, 436 before they are provided to detectors 406, 408, so that emissions only within an emission band (i.e., a subset of the entire spectrum) actually impinges upon the active area of each detector 406, 408. The spectral filters 410, 412 may include, for example, long pass, bandpass, or other types of filters configured to pass light only within a spectral band of interest, and to reject all other light.

Each of detectors 406, 408 has sensitivity within a spectral band of interest, and accordingly may detect light passing through the spectral filter 410, 412 that is within that spectral band. According to an embodiment, detector 406 is configured to detect emissions within a channel corresponding to a first band of interest (the overlapping or confounded emission band) associated with the substrate and extrinsic feature emissions. In contrast, detector 408 is configured to detect emissions within a channel corresponding to a second band of interest (the supplemental emission band) associated with the non-overlapping supplemental emissions. The detectors 406, 408 may be of the same type or of different types. According to a particular embodiment, the detectors 406, 408 are of different types. For example, one of detectors 406, 408 may include a silicon detector, and the other of detectors 406, 408 may include an indium-gallium-arsenide (InGaAs) detector (e.g., a telecom type or extended InGaAs). Other types of detectors may that are capable of detecting emissions within a band of interest may be used, in other embodiments (e.g., lead-sulfide, lead-selenide, germanium, indium-antimonide, indium-arsenide, platinum-silicide, indium-antimonide, and so on). In an alternate embodiment, a single detector may be employed, which is capable of detecting emissions in all bands of interest. In such an embodiment, signal splitter/dispersion element 414 may be excluded from system 400. In other alternate embodiments, more than two detectors may be employed to detect emissions in more than two bands of interest. In such embodiments, a plurality of signal splitter/dispersion elements may be employed to direct extrinsic beams toward the multiple detectors.

Each detector 406, 408 produces an electronic signal that is proportional to the intensity of the collected radiation that impinges on the active area of the detector 406, 408. More particularly, each detector 406, 408 produces a signal (e.g., one or more digitized intensity values) representing an integrated intensity of the emissions received by the detector 406, 408 along substantially all or a portion of the length of the article (e.g., between an incident and trailing edge of the article). Desirably, when multiple detectors 406, 408 are used in the system (e.g., as in the system 400 of FIG. 4), the values of the integrated intensity are electronically captured by each detector 406, 408 at the same time, although this is not a requirement.

Each emissions detector 406, 408 may digitize intensity values at one or more pre-selected intervals (e.g., starting at t=0, and then every 0.1 milliseconds thereafter, for several intervals). In addition, each emissions detector 406, 408 provides information to processing system 402 (e.g., the digitized intensity values), which enables the temporal, spectral, and positional properties of the emissions 428 to be characterized. For example, emissions detector 406 produces a series of values corresponding to intensities of emitted radiation in the confounded emission band. Each value or sets of values from detector 406 may be tagged or otherwise associated with information indicating a location of the detected emissions (e.g., a linear distance from the incident edge of the article) and a time when the emissions were detected (e.g., a time from discontinuation of provision of the corresponding excitation energy). Similarly, emissions detector 408 produces a series of values corresponding to intensities of emitted radiation in the supplemental emission band. As with the values produced by emissions detector 406, each value or sets of values from detector 408 may be tagged or otherwise associated with information indicating a location of the detected emissions and a time when the emissions were detected.

Processing system 402 is configured to analyze such information, upon its receipt, in order to determine whether or not the temporal, spectral, and positional properties of any detected radiation correspond to the temporal, spectral, and positional properties of an authentic article. As will be described in more detail in conjunction with FIG. 5, authenticating parameters for the system 400 include parameters selected from a group consisting of: emission intensities (or integrated intensities) in the confounded emission band across all or one or more portions of the length of the article; emission intensities (or integrated intensities) in the supplemental emission band across all or one or more portions of the length of the article; emission decay time constant in the confounded emission band across all or one or more portions of the length of the article; emission decay time constant in the supplemental emission band across all or one or more portions of the length of the article; emission rise time constant in the confounded emission band across all or one or more portions of the length of the article; emission rise time constant in the supplemental emission band across all or one or more portions of the length of the article; ratio of emission intensities (or integrated intensities) between emissions in the confounded band and emissions in another band; and ratio of emission intensities (or integrated intensities) between emissions in the supplemental band and emissions in another band. Additional authenticating parameters may be defined, as well.

Ranges of authenticating parameters that correspond with an authentic article define the detection parameter space of the system 400. In an embodiment, processing system 402 determines whether the values produced by detectors 406, 408 for the authenticating parameters fall within the detection parameter space. In other words, processing system 402 compares the values with ranges defining the detection parameter space to determine whether the values fall within those ranges. For example, regarding the authentication parameter corresponding to the emission intensities in the confounded emission band across all or one or more portions of the length of the article, a table of intensity value ranges may be defined for each possible article orientation. In order to analyze a particular intensity value (e.g., an intensity value from detector 406, which is tagged with a location where the emission intensity was detected and a time), processing system 402 may retrieve a pre-defined intensity range from the table (e.g., a range corresponding to the location and time associated with the intensity value), and may compare the intensity value with the range to determine whether the value falls within the range. Such analyses may be performed for intensity values at multiple locations along the length of the article. Values corresponding to the other authentication parameters may be similarly analyzed.

When the analysis indicates that the values corresponding with the authenticating parameters fall within the detection parameter space to within an acceptable degree of accuracy, processing system 402 may identify the article 450 as being authentic. Conversely, the analysis indicates that the values corresponding with the authenticating parameters do not fall within the detection parameter space to within an acceptable degree of accuracy, processing system 402 is configured to identify the article 450 as being unauthentic.

When the temporal, spectral, and positional properties of detected radiation correspond with an authentic article, processing system 402 may take some action associated with identifying article 450 as an authentic article. For example, processing system 402 may send an electronic signal associated with authenticity to another component of the system or to an external system. In addition, processing system 402 may send a signal to user interface 418, which causes user interface 418 to produce a user-perceptible indication of authenticity (e.g., a displayed indicia, a light, a sound, and so on). Processing system 402 also may cause a routing component of system 400 (not illustrated) to route article 450 toward a route or bin assigned for authentic articles. Alternatively, when the temporal and/or spectral properties of the detected radiation do not correspond with an authentic article, processing system 402 may take some action associated with identifying article 450 as an unauthentic article. For example, processing system 402 may send an electronic signal associated with unauthenticity to another component of the system or to an external system. In addition, processing system 402 may send a signal to user interface 418, which causes user interface 418 to produce a user-perceptible indication of unauthenticity (e.g., a displayed indicia, a light, a sound, and so on). Processing system 402 also may cause a routing component of system 400 (not illustrated) to route article 450 toward a route or bin assigned for unauthentic articles.

User interface 418 may include any of a number of components that may be manipulated by a user to provide inputs to system 400 (e.g., keyboards, buttons, touchscreens, and so on), or which may be controlled by processing system 402 to produce user-perceptible indicia (e.g., display screens, lights, speakers, and so on). The above-described process may be initiated in response to user inputs provided through the user's interaction with user interface 418, for example. Alternatively, the above-described process may be initiated automatically by the system 400, such as when the article 450 has been positioned in a location at which the excitation and detection processes may be performed.

Figure 5:
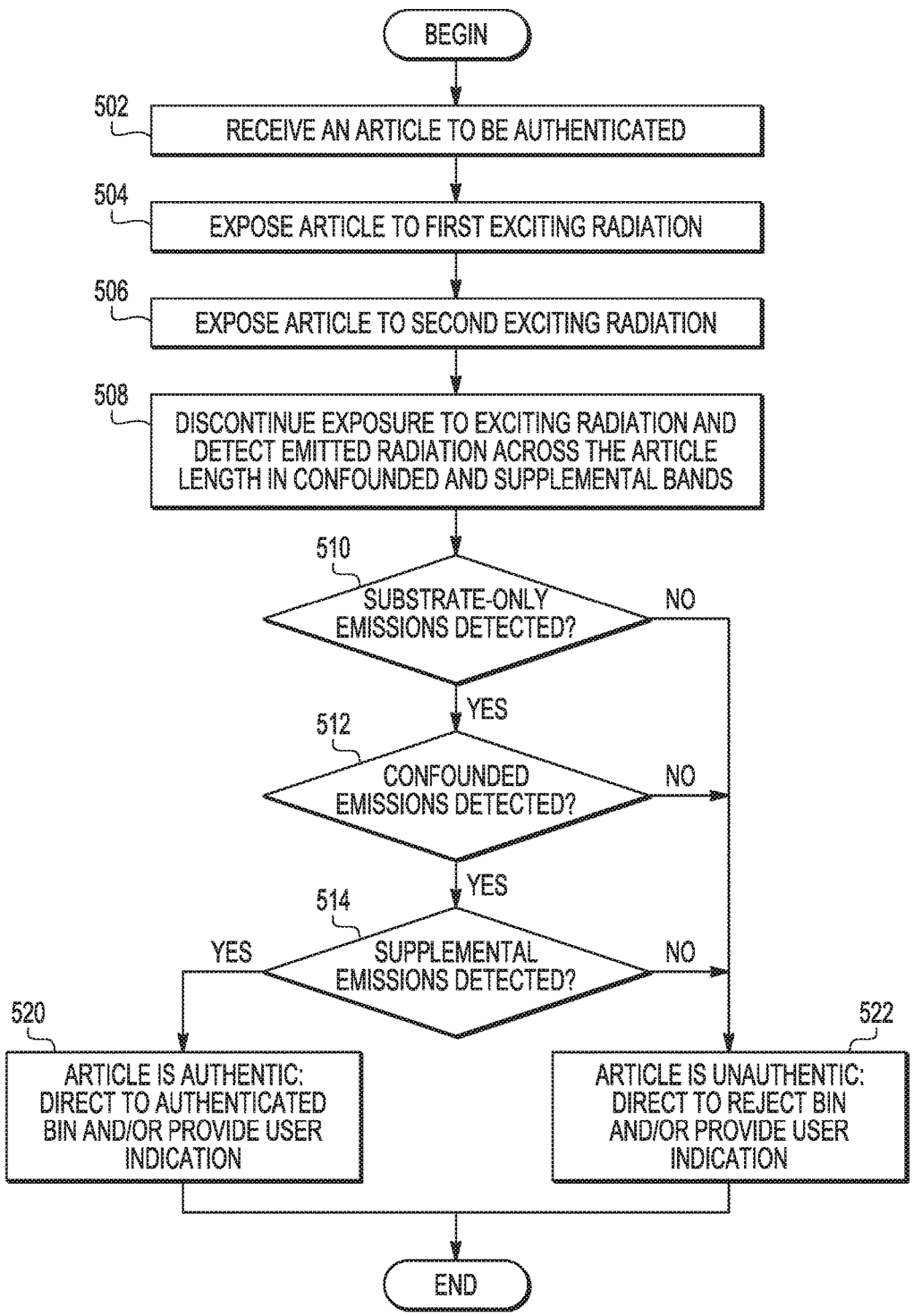
FIG. 5 is a flowchart of a method for performing authentication of an article, in accordance with an example embodiment.

FIG. 5 is a flowchart of a method for performing authentication of an article (e.g., article 100, FIG. 1 or article 450, FIG. 4), in accordance with an example embodiment. For example, embodiments of the method depicted in FIG. 5 may be performed by an authentication system (e.g., authentication system 400, FIG. 4). The method may begin, in block 502, when an article to be authenticated (e.g., article 450, FIG. 4) is received by the authentication system. For example, an article may be routed (e.g., by a sorting or conveyor system) into the authentication system in a known or unknown orientation with an incident edge of the article first entering the authentication system. As another example, the article may be placed into an appropriate receptacle of the authentication system.

In block 504, the article is exposed to first excitation energy associated with a substrate taggant and an extrinsic feature taggant (e.g., taggants 130, 132, FIG. 1). For example, the article may be routed to or past an excitation area (e.g., under excitation window 424, FIG. 4), and the processing system (e.g., processing system 402, FIG. 4) may send a control signal to an excitation energy generator (e.g., excitation energy generator 404, FIG. 4) that causes the excitation energy generator to direct the first excitation energy (e.g., excitation energy 420, FIG. 4) toward the article. Alternatively, the excitation energy generator may continuously provide the first excitation energy or the first excitation energy may be modulated. In various embodiments, excitation may be provided using a filtered LED, a laser diode or another optical excitation source capable of producing excitation energy in a desired wavelength band.

In block 506, which may be performed concurrently with block 504 or at some other time, the article optionally is exposed to second excitation energy associated with a supplemental taggant (e.g., taggant 134, FIG. 1). For example, the processing system (e.g., processing system 402, FIG. 4) may send a control signal to the same excitation energy generator or to another excitation energy generator that causes the excitation energy generator to direct the second excitation energy (e.g., excitation energy 422, FIG. 4) toward the article. Alternatively, the excitation energy generator may continuously provide the second excitation energy or the second excitation energy may be modulated. Block 506 may be excluded when a supplemental taggant is not implemented, or when the excitation energy for the supplemental taggant is the same as the supplemental energy for the substrate and/or extrinsic feature taggants.

In block 508, provision of the first and second excitation energy to the article is discontinued, and the authentication system detects emissions within multiple bands from the article (e.g., by emissions detectors 406, 408, FIG. 4). Discontinuation of the excitation energy may be accomplished either by turning the excitation energy generators off (e.g., in a system in which the article may remain stationary and the excitation energies are pulsed), or by routing the article away from the area where the excitation energies are being directed, and to a detection area (e.g., under detection window 432, FIG. 4). In an alternate embodiment, provision of the excitation energies may continue while the system performs the detection processes described below.

Emissions detection may be performed at one or more detection intervals, which are measured from the time that direction of the excitation energies toward the article was discontinued. According to an embodiment, the system is configured to detect emissions in at least a first band and a second band, although the system may be configured to detect emissions in more than two bands, as well. The first band corresponds to overlapping bands associated with emissions produced by the substrate taggant (e.g., taggant 130, FIG. 1) and the extrinsic feature taggant (e.g., taggant 132, FIG. 1). More particularly, the first band corresponds to the confounded emission band (i.e., the band at which the substrate taggant emissions and the extrinsic feature emissions overlap). The second band corresponds to a band associated with emissions produced by the supplemental taggant (i.e., the supplemental band).

In blocks 510-514, which may be performed sequentially or in parallel, information quantizing the intensities of detected emissions within the multiple bands is analyzed (e.g., by processing system 402, FIG. 4). According to an embodiment, the information includes one or more series of digitized intensity values (e.g., from each of detectors 406, 408, FIG. 4) corresponding to intensities of emitted radiation in the confounded and supplemental emission bands. As discussed previously, individual values or sets of values may be tagged or otherwise associated with information indicating a location of the detected emissions and a time when the emissions were detected. The digitized intensity values represent the temporal and/or positional properties of the detected emissions in the confounded and supplemental emission bands.

In block 510, a determination is made whether emissions having characteristics of substrate-only emissions are detected in one or more first regions of the article (e.g., in regions that are substrate-only regions (e.g., region 162, FIG. 1) in an authentic article). This determination is made based on digitized intensity values received from a detector (e.g., detector 406, FIG. 4) configured to detect emissions in the confounded emission band. According to an embodiment, emission properties in the confounded emission band may be analyzed by determining appropriate authenticating parameter ranges (e.g., emission intensity ranges) for a substrate-only region at a time corresponding to the time when the digitized intensity values were produced. For example, as discussed previously, appropriate authenticating parameter ranges may be maintained by the authentication system in one or more tables that define the detection parameter space. In an embodiment, a multiple orientation analysis may be performed by correlating multiple (e.g., up to four) of such ranges with the digitized intensity values, where the multiple ranges correspond with multiple possible orientations of the article.

When a digitized intensity value falls within an appropriate authenticating parameter range for the region and time associated with the value, a determination may be made that an emission having characteristics of a substrate-only emission has been detected. Otherwise, when a digitized intensity value falls outside the appropriate authenticating parameter range (or all of the authenticating parameter ranges when multiple orientation analysis is performed) for the region and time associated with the value, a determination may be made that an emission having characteristics of a substrate-only emission has not been detected. According to an embodiment, multiple digitized intensity values may be analyzed in the first region, and the determination may allow one or more of the intensity values to fall outside the appropriate authenticating parameter range, while still yielding a positive result. In other words, the determination may be made to within an acceptable degree of accuracy. When a determination is made that emissions having characteristics of substrate-only emissions have not been detected in one or more first regions of the article (i.e., the analysis indicates that the intensity values do not fall within the detection parameter space to within an acceptable degree of accuracy), the system may identify the article as being unauthentic, and may take a corresponding action in block 522, which is described in more detail below.

In block 512, a determination is made whether emissions having characteristics of confounded emissions are detected in one or more second regions of the article (e.g., in regions that are extrinsic feature regions (e.g., region 164, FIG. 1) in an authentic article). Again, this determination is made based on digitized intensity values received from a detector (e.g., detector 406, FIG. 4) configured to detect emissions in the confounded emission band. According to an embodiment, emission properties in the confounded emission band may be analyzed by determining appropriate authenticating parameter ranges (e.g., emission intensity ranges) for an extrinsic feature region at a time corresponding to the time when the digitized intensity values were produced, as discussed above.

When a digitized intensity value falls within an appropriate authenticating parameter range for the region and time associated with the value, a determination may be made that an emission having characteristics of a confounded emission has been detected. Otherwise, when a digitized intensity value falls outside the appropriate authenticating parameter range (or all of the authenticating parameter ranges when multiple orientation analysis is performed) for the region and time associated with the value, a determination may be made that an emission having characteristics of a confounded emission has not been detected. According to an embodiment, the determination may be made to within an acceptable degree of accuracy, as previously described. When a determination is made that emissions having characteristics of confounded emissions have not been detected in one or more second regions of the article (i.e., the analysis indicates that the intensity values do not fall within the detection parameter space to within an acceptable degree of accuracy), the system may identify the article as being unauthentic, and may take a corresponding action in block 522, which is described in more detail below.

In block 514, which may be performed in an embodiment in which a supplemental taggant is incorporated into an article, a determination is made whether emissions having characteristics of supplemental emissions are detected in one or more regions of the article (e.g., in regions in which a supplemental taggant (e.g., taggant 134, FIG. 1) is present in an authentic article). Again, this determination is made based on digitized intensity values received from a detector (e.g., detector 408, FIG. 4) configured to detect emissions in the supplemental emission band. According to an embodiment, emission properties in the supplemental emission band may be analyzed by determining appropriate authenticating parameter ranges (e.g., emission intensity ranges) for a supplemental taggant at a time corresponding to the time when the digitized intensity values were produced, as discussed above.

When a digitized intensity value falls within an appropriate supplemental taggant range for the region and time associated with the value, a determination may be made that an emission having characteristics of a supplemental emission has been detected. Otherwise, when a digitized intensity value falls outside the appropriate supplemental taggant range (or all of the supplemental taggant ranges when multiple orientation analysis is performed) for the region and time associated with the value, a determination may be made that an emission having characteristics of a supplemental emission has not been detected. According to an embodiment, the determination may be made to within an acceptable degree of accuracy, as previously described. When a determination is made that emissions having characteristics of supplemental emissions have not been detected in one or more regions of the article (i.e., the analysis indicates that the intensity values do not fall within the detection parameter space to within an acceptable degree of accuracy), the system may identify the article as being unauthentic, and may take a corresponding action in block 522, which is described in more detail below.

According to an embodiment, analysis of the substrate-only, confounded, and supplemental emissions includes analysis of the intensities (or integrated intensities) of the emissions. Accordingly, the appropriate authenticating parameter ranges include emission intensity ranges, as described above. In another embodiment, analysis of the substrate-only, confounded, and supplemental emissions also or alternatively may include determining the decay time of emissions within the confounded and supplemental bands. Accordingly, the appropriate authenticating parameter ranges also or alternatively may include decay time constant ranges. In an embodiment, the decay time(s) may be determined based on the detected intensities of the emissions at multiple times (e.g., t=0, t=0.1 millisecond, and so on). Upon removal of the excitation energy, the intensity of the emission decays over time, and the rate of decay for the emitting ion can be characterized by the decay time constant. For example, for a simple exponential decay in emission intensity, the decay time constant can be represented by the constant $\tau$ in the equation:

$$I(t)=I_0 e^{-t/\tau}, \quad \text{(Equation 1)}$$

where t denotes time, I(t) denotes the emission intensity at time t, and $I_0$ denotes the emission intensity at t=0 (e.g., t=0 may correspond to the instant when the provision of excitation energy is discontinued). Although the emission intensity for some luminescent materials may decay according to the above, simple exponential formula, the emission intensity for other luminescent materials may be affected by multiple exponential decays (e.g., when multiple mechanisms affecting the decay are present). In some cases, a luminescent material may not exhibit a simple single exponential decay, especially when energy transfer is part of the mechanism.

When each of the determinations in blocks 510, 512, and 514 yield positive results (i.e., substrate-only, confounded, and supplemental emissions each were appropriately detected), then in block 520, the system may identify the article as being "authentic," and may take a corresponding action. For example, the system may produce a user-perceptible indication of authenticity, and/or may cause a routing component of the system to route the article toward a route or bin assigned for authentic articles. Alternatively, when one or more of the determinations in blocks 510, 512, and 514 yield negative results (i.e., substrate-only, confounded, and/or supplemental emissions were not appropriately detected), the system may identify the article as being "unauthentic," and may take a corresponding action, in block 522. For example, the system may produce a user-perceptible indication of unauthenticity, and/or may cause a routing component of the system to route the article toward a route or bin assigned for unauthentic articles.

Figure 6:
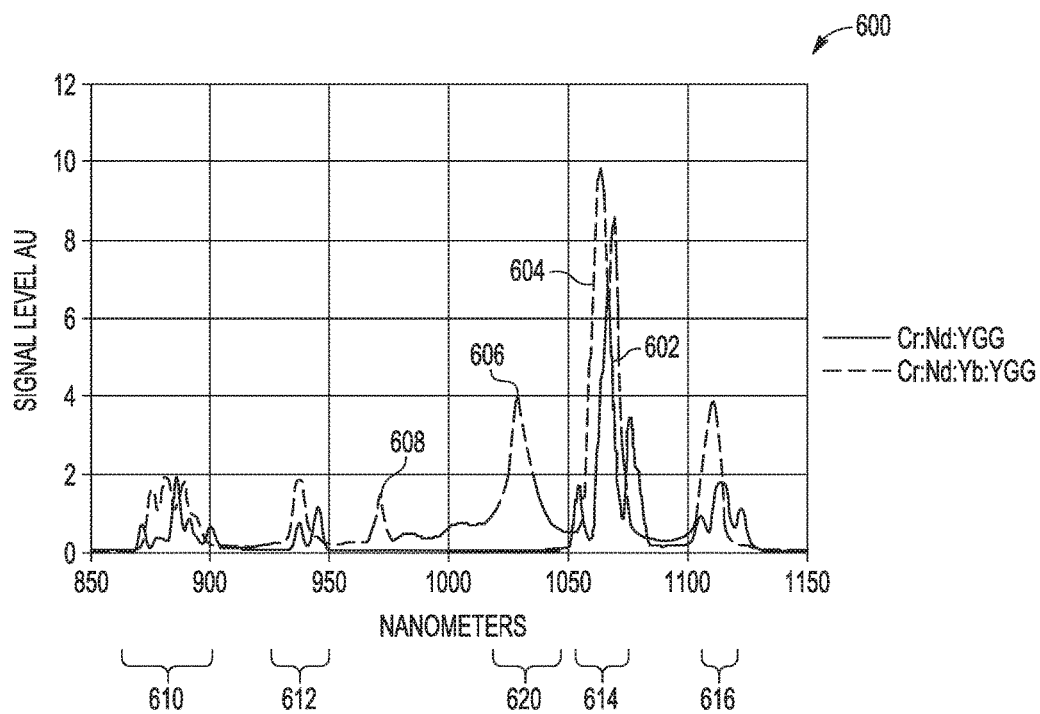
FIG. 6 is a graph illustrating emission intensities of various taggants at multiple wavelengths in both a substrate-only region and an extrinsic feature region of an article, according to an example embodiment.

FIG. 6 is a graph 600 emulating emission intensities of various taggants at multiple wavelengths in both a substrate-only region and an extrinsic feature region of an article, according to an example embodiment. In the example, a substrate taggant was included in an article substrate, and an extrinsic feature taggant was included in a media (e.g., ink) printed on top of a substrate surface. The substrate taggant produced emissions 602 (e.g., emulating emissions perceptible in a substrate-only region of an article), and the combination of the substrate taggant and the extrinsic feature taggant produced emissions 604 (e.g., emulating emissions perceptible in an extrinsic feature region of an article).

To generate the graph 600, first test samples without extrinsic features were produced. More particularly, a substrate taggant material comprising Cr:Nd:YGG (with the Cr at 20 wt % and the Nd at 0.7 wt % in the host lattice material YGG) was added to a paper handsheet article substrate. To produce emissions 602 from the first test samples, an LED was used to excite the substrate taggant material into the chromium absorption band (typically at 660 nm), and emissions 602 were detected.

Second test samples with extrinsic features also were produced. More particularly, an ink was created that included an ink base and an extrinsic feature taggant material comprising Cr:Nd:Yb:YGG (with the Cr at 20 wt %, the Nd at 0.7 wt %, and the Yb at 0.5 wt % in the host lattice material YGG). The ink was printed on a surface of a paper handsheet substrate that included the substrate taggant material. To produce emissions 604 from the second test samples, an LED was used to excite both the substrate taggant material and the extrinsic feature taggant material into the chromium absorption band, resulting in confounded emissions due to overlapping neodymium emissions from the substrate and extrinsic feature in band 610 (at ~870-905 nm), band 612 (at ~930-950 nm), band 614 (at ~1055-1070 nm), and band 616 (at ~1110-1120 nm).

As is indicated, a distinction between the extrinsic feature taggant material and the substrate taggant material was that the extrinsic feature taggant material contained ytterbium, and the substrate taggant material did not. In the extrinsic feature taggant, the presence of the ytterbium in the YGG lattice distorted the lattice structure slightly, so the confounded peaks in emissions 604 did not exhibit exactly the same band emission as the peaks in emissions 602 from the substrate taggant alone. This satisfies the criteria for confounded emission.

The ytterbium present in the extrinsic feature taggant also functioned as a supplemental ion that produced supplemental emissions. More particularly, supplemental band emissions (e.g., in supplemental band 620) were present from the extrinsic feature taggant material due to the presence of ytterbium. According to an embodiment, it is possible to excite a supplemental ion (e.g., the ytterbium) alone in an extrinsic feature material (e.g., using supplemental excitation energy at about 970 nm) to produce supplemental emissions in a supplemental band (e.g., band 620). In the example, if the ytterbium is excited alone (i.e., the neodymium is not excited), the confounded emissions may not be present. In FIG. 6, a major peak 606 corresponding to supplemental band 620 is centered primarily at about 1030 nm, and a minor peak 608 is centered at about 970 nm.

Figure 7:
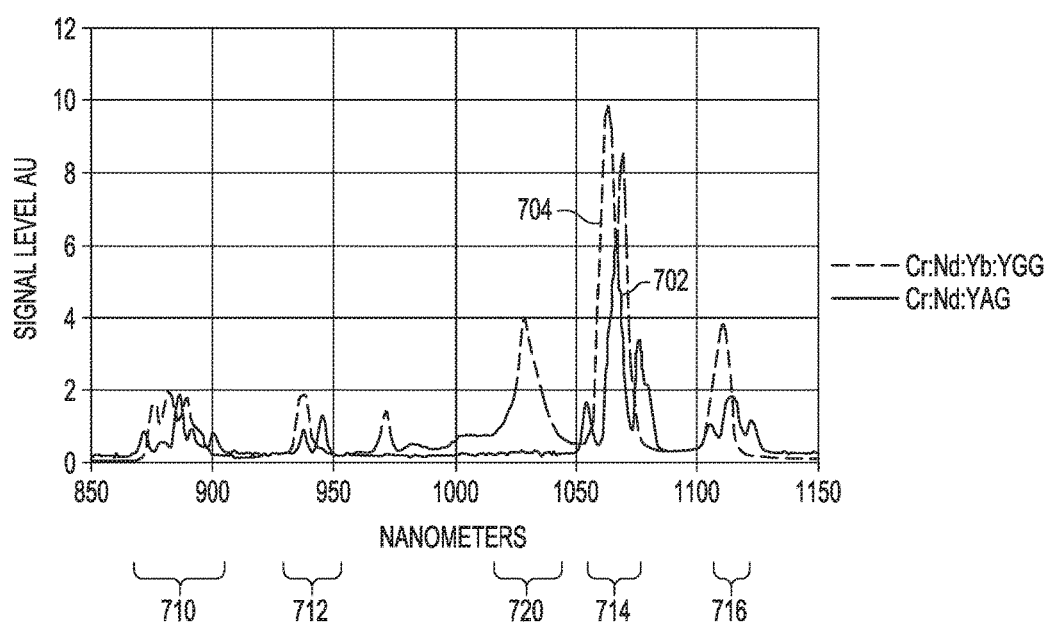
FIG. 7 is a graph illustrating emission intensities of various taggants at multiple wavelengths in both a substrate-only region and an extrinsic feature region of an article, according to another example embodiment.

FIG. 7 is a graph 700 emulating emission intensities of various taggants at multiple wavelengths in both a substrate-only region and an extrinsic feature region of an article, according to another example embodiment. A main distinction between the example of FIG. 6 and the example of FIG. 7 is that the substrate taggant material responsible for emissions 602 in FIG. 6 included YGG as the host material, whereas the substrate taggant material responsible for emissions 702 in FIG. 7 included YAG as the host material. In both examples, however, the host material for the extrinsic feature taggant included YAG. The example of FIG. 7 is provided to illustrate that the host material for the substrate taggant and the extrinsic feature taggant need not be the same.

As with the previous example of FIG. 6, in the example of FIG. 7, a substrate taggant was included in the article substrate, and a extrinsic feature taggant was included in a media (e.g., ink) printed on top of a substrate surface. The substrate taggant produced emissions 702 (e.g., emulating emissions perceptible in a substrate-only region of an article), and the combination of the substrate taggant and the extrinsic feature taggant produced emissions 704 (e.g., emulating emissions perceptible in an extrinsic feature region of an article).

To generate the graph 700, third test samples without extrinsic features were produced. More particularly, a substrate taggant material comprising Cr:Nd:YAG (with the Cr at 20 wt % and the Nd at 0.7 wt % in the host lattice material YAG) was added to a paper handsheet article substrate. To produce emissions 702 from the third test samples, an LED was used to excite the substrate taggant material into the chromium absorption band (typically at 660 nm), and emissions 702 were detected.

Fourth test samples with extrinsic features also were produced. More particularly, an ink was created that included an ink base and a multiple band feature taggant material comprising Cr:Nd:Yb:YGG (with the Cr at 20 wt %, the Nd at 0.7 wt %, and the Yb at 0.5 wt % in the host lattice material YGG). The ink was printed on a surface of a paper handsheet substrate that included the substrate taggant material. To produce emissions 704 from the second test samples, an LED was used to excite both the substrate taggant material and the extrinsic feature taggant material into the chromium absorption band, resulting in confounded emissions in band 710 (at ~870-905 nm), band 712 (at ~930-950 nm), band 714 (at ~1055-1070 nm), and band 716 (at ~1110-1120 nm).

Once again, in the extrinsic feature taggant, the presence of the ytterbium in the YGG lattice distorted the lattice structure slightly, so the confounded peaks in emissions 704 did not exhibit exactly the same band emission as the peaks in emissions 702 from the substrate taggant alone. In addition, the ytterbium produced the supplemental emissions in supplemental band 720.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for authenticating an article that includes a substrate, the method comprising the steps of:
   exposing a surface of the substrate to excitation energy;
   determining whether, in a first region of the surface, first emissions having first emission characteristics are detected in a first emission band, wherein the first emissions result from the excitation energy, and the first region corresponds to a region at which an extrinsic feature is not present in an authentic article;
   determining whether, at a second region of the surface, second emissions having second emission characteristics that are different from the first emission characteristics are detected in the first emission band, wherein the second emissions result from the excitation energy, and the second region corresponds to a region at which the extrinsic feature is present in the authentic article; and
   identifying the article as authentic or unauthentic based on the detection of the first emission and the second emission in the first emission band.

2. The method of claim 1, further comprising:
   identifying the article as being authentic when the first and second emissions are detected, and when the second emissions have the second emission characteristics; and
   identifying the article as being unauthentic when the first emissions, the second emissions or both are not detected, or when the second emissions do not have the second emission characteristics.

3. The method of claim 2, further comprising:
   determining a location of the second region with respect to the surface;
   determining whether the location corresponds to a location of the extrinsic feature on the authentic article;
   when the location of the second region corresponds to the location of the extrinsic feature, identifying the article as being authentic; and
   when the location of the second region does not correspond to the location of the extrinsic feature, identifying the article as being unauthentic.

4. The method of claim 1, wherein exposing the surface of the substrate to excitation energy comprises:
   exposing the surface to excitation energy at a wavelength that results in energy absorption by a first emitting ion of a first taggant incorporated into a substrate of an authentic article and that also results in energy absorption by a second emitting ion of a second taggant incorporated into an extrinsic feature of the authentic article.

5. The method of claim 1, wherein exposing the surface of the substrate to excitation energy comprises:
   exposing the surface to excitation energy at a first wavelength that results in energy absorption by a first emitting ion of a first taggant incorporated into a substrate of an authentic article; and
   exposing the surface to excitation energy at a second wavelength that results in energy absorption by a second emitting ion of a second taggant incorporated into an extrinsic feature of an authentic article, wherein the second wavelength is different from the first wavelength.

6. The method of claim 1, wherein the second emission characteristics are different from the first emission characteristics in that a second emission intensity is perceptibly different from a first emission intensity.

7. The method of claim 1, wherein the second emission characteristics are different from the first emission characteristics in that a second decay time constant is perceptibly different from a first decay time constant.

8. The method of claim 1, wherein exposing the surface of the substrate to excitation energy comprises:
   exposing the surface to first excitation energy at one or more wavelengths that result in energy absorption by an emitting ion of a first taggant incorporated into the substrate of the authentic article and that result in energy absorption by an emitting ion of a second taggant incorporated into the extrinsic feature of the authentic article, and
   exposing the surface to second excitation energy at a wavelength that results in energy absorption by a supplemental ion incorporated into the authentic article;
   and the method further comprises:
   determining whether supplemental emissions are detected in a second emission band that is different from the first emission band, wherein the supplemental emissions result from the second excitation energy.

9. The method of claim 1, wherein exposing the surface of the substrate to excitation energy comprises:
   exposing the first region of the surface to substrate excitation energy that results in energy absorption by a first luminescent taggant incorporated into the substrate of the authentic article; and
   exposing the second region of the surface to extrinsic feature excitation energy that results in energy absorption by a second luminescent taggant incorporated into the extrinsic feature of the authentic article, wherein the extrinsic feature is positioned proximate the first region of the substrate at which the first luminescent taggant is present.

10. The method of claim 9, wherein the first luminescent taggant produces the first emissions in the first emission band when the substrate is exposed to the substrate excitation energy and wherein the second luminescent taggant produces the second emissions having the second emission characteristics when the extrinsic feature is exposed to the extrinsic feature excitation energy, wherein the second emissions have a second emission band at least partially overlapping the first emission band in an overlapping emission band, and wherein the method further comprises detecting the first emissions from the first region and emissions from the second region within a detection channel that corresponds to the overlapping emission band.

11. The method of claim 10, wherein determining whether, at the second region of the surface, the second emissions are detected in the first emission band comprises determining whether the first emissions and the second emissions have distinguishable emission characteristics from each other.

12. The method of claim 10, wherein the first emissions and the second emissions combine in the overlapping emission band to produce confounded emissions that are distinguishable from the first emissions, where the confounded emissions have emission characteristics that are distinguishable from the first emissions from the first luminescent taggant and from the second emissions from the second luminescent taggant, taken separately, and wherein determining whether, at the second region of the surface, the second emissions are detected in the first emission band comprises determining whether the confounded emissions are detected in the overlapping emission band.

13. The method of claim 12, wherein when a determination is made that emissions having characteristics of confounded emissions have not been detected in one or more second regions of the article, the article is identified as being unauthentic.

14. The method of claim 10, further comprising detecting the first emissions and the second emissions with a detector configured to detect emissions within a channel corresponding to the overlapping emission band.

15. An apparatus for authenticating an article that includes a substrate, the apparatus comprising:
one or more excitation energy generators configured to direct excitation energy toward a surface of the substrate;
a first emissions detector configured to detect first emissions in a first emission band; and
a processing system configured to determine whether, in a first region of the surface, first emissions having first emission characteristics are detected in a first emission band, wherein the first emissions result from the excitation energy, and the first region corresponds to a region at which an extrinsic feature is not present in an authentic article, wherein the processing system is further configured to determine whether, at a second region of the surface, second emissions having second emission characteristics that are different from the first emission characteristics are detected in the first emission band, wherein the second emissions result from the excitation energy, and the second region corresponds to a region at which the extrinsic feature is present in the authentic article, and wherein the processing system is further configured to identify the article as authentic or unauthentic based on detection of the first emission and the second emission in the first emission band.

16. The apparatus of claim 15, wherein the at least one excitation energy generator is configured to expose the surface of the substrate to excitation energy by exposing the surface to excitation energy at a wavelength that results in energy absorption by a first emitting ion of a first taggant incorporated into a substrate of an authentic article and that also results in energy absorption by a second emitting ion of a second taggant incorporated into an extrinsic feature of the authentic article.

17. The apparatus of claim 15, wherein the at least one excitation energy generator is configured to expose the surface of the substrate to excitation energy by:
exposing the surface to excitation energy at a first wavelength that results in energy absorption by a first emitting ion of a first taggant incorporated into a substrate of an authentic article; and
exposing the surface to excitation energy at a second wavelength that results in energy absorption by a second emitting ion of a second taggant incorporated into an extrinsic feature of an authentic article, wherein the second wavelength is different from the first wavelength.

18. The apparatus of claim 15, wherein:
the at least one excitation energy generator is configured to expose the surface of the substrate to excitation energy by exposing the surface to first excitation energy at one or more wavelengths that result in energy absorption by an emitting ion of a first taggant incorporated into the substrate of the authentic article and that result in energy absorption by an emitting ion of a second taggant incorporated into the extrinsic feature of the authentic article;
the at least one excitation energy generator is further configured to expose the surface to second excitation energy at a wavelength that results in energy absorption by a supplemental ion;
the apparatus further comprises a second emissions detector configured to detect emissions in a supplemental emission band that does not overlap the first emission band; and
the processing system is further configured to:
determine whether, supplemental emissions are detected in a second emission band that is different from the first emission band, wherein the supplemental emissions result from the second excitation energy.

* * * * *